(12) United States Patent
Chavarria

(10) Patent No.: US 9,370,346 B2
(45) Date of Patent: Jun. 21, 2016

(54) METHOD AND APPARATUS FOR CONTAINING, TRANSPORTING, AND PROVIDING A MATERIAL

(71) Applicant: Biomet Biologics, LLC, Warsaw, IN (US)

(72) Inventor: Jason Chavarria, Warsaw, IN (US)

(73) Assignee: BIOMET BIOLOGICS, LLC, Warsaw, IN (US)

( * ) Notice: Subject to any disclaimer, the term of this patent is extended or adjusted under 35 U.S.C. 154(b) by 0 days.

(21) Appl. No.: 14/015,205

(22) Filed: Aug. 30, 2013

(65) Prior Publication Data
US 2014/0012315 A1    Jan. 9, 2014

Related U.S. Application Data

(62) Division of application No. 12/260,541, filed on Oct. 29, 2008, now Pat. No. 8,523,805.

(51) Int. Cl.
*A61M 31/00* (2006.01)
*A61B 17/00* (2006.01)

(52) U.S. Cl.
CPC . *A61B 17/00491* (2013.01); *A61B 2017/00495* (2013.01)

(58) Field of Classification Search
CPC ............... A61B 17/00491; A61B 2017/00495; A61M 31/00
See application file for complete search history.

(56) References Cited

U.S. PATENT DOCUMENTS

| | | | |
|---|---|---|---|
| 1,474,603 A | 11/1923 | Morse | |
| 1,950,137 A | 3/1934 | Dowe | |
| 3,323,550 A | 6/1967 | Lee, II | |
| 3,717,306 A | 2/1973 | Hushon et al. | |
| 3,746,216 A | 7/1973 | Frederick | |
| 3,749,084 A | 7/1973 | Cucchiara | |
| 3,753,527 A | 8/1973 | Galbraith et al. | |
| 3,945,574 A | 3/1976 | Polnauer et al. | |
| 4,359,049 A | 11/1982 | Redl et al. | |
| 4,609,371 A | 9/1986 | Pizzino | |
| 4,874,368 A | 10/1989 | Miller et al. | |

(Continued)

FOREIGN PATENT DOCUMENTS

| | | |
|---|---|---|
| EP | 0294672 A1 | 12/1988 |
| EP | 0689874 A1 | 8/2006 |

(Continued)

OTHER PUBLICATIONS

European Office Communication dated May 27, 2013 for European Application No. 097479866.1 (based on PCT/US/2009/062298 filed Oct. 28, 2009); 7 pages (2013).

(Continued)

*Primary Examiner* — Imani Hayman
(74) *Attorney, Agent, or Firm* — Schwegman Lundberg & Woessner, P.A.

(57) ABSTRACT

A method for expressing two materials onto a selected site is disclosed. The method can include providing a syringe that is operable to maintain two separated materials substantially separate until a selected time. The method can further include mounting a tip portion to the syringe, the tip portion being operable to direct the two materials, either mixed or unmixed, to a selected site. The materials can include tissue sealants, growth factors, or other appropriate materials to be directed to a selected site.

20 Claims, 15 Drawing Sheets

(56) References Cited

U.S. PATENT DOCUMENTS

| | | |
|---|---|---|
| 4,978,336 A | 12/1990 | Capozzi et al. |
| 4,979,942 A | 12/1990 | Wolf et al. |
| 5,242,300 A | 9/1993 | Esrock |
| 5,322,510 A | 6/1994 | Lindner et al. |
| 5,368,563 A | 11/1994 | Lonneman et al. |
| 5,413,253 A | 5/1995 | Simmen |
| 5,605,255 A | 2/1997 | Reidel et al. |
| 5,605,541 A | 2/1997 | Holm |
| 5,609,271 A | 3/1997 | Keller et al. |
| 5,665,067 A | 9/1997 | Linder et al. |
| 5,792,103 A | 8/1998 | Schwartz et al. |
| 5,814,022 A | 9/1998 | Antanavich et al. |
| 5,975,367 A | 11/1999 | Coelho et al. |
| 5,989,215 A | 11/1999 | Delmotte et al. |
| 5,997,811 A | 12/1999 | Esposito |
| 6,045,058 A | 4/2000 | Dobbeling et al. |
| 6,132,396 A | 10/2000 | Antanavich et al. |
| 6,148,536 A | 11/2000 | Iijima |
| 6,234,795 B1 | 5/2001 | Fischer |
| 6,328,229 B1 | 12/2001 | Duronio et al. |
| 6,461,325 B1 | 10/2002 | Delmotte et al. |
| 6,629,947 B1 | 10/2003 | Sahatjian et al. |
| 6,705,756 B2 | 3/2004 | Botrie et al. |
| 6,773,414 B2 | 8/2004 | Ljungquist |
| 6,835,186 B1 | 12/2004 | Pennington et al. |
| 6,921,380 B1 | 7/2005 | Epstein et al. |
| 7,018,357 B2 | 3/2006 | Emmons |
| 8,523,805 B2 | 9/2013 | Chavarria |
| 2007/0083155 A1 | 4/2007 | Muller |
| 2007/0191781 A1 | 8/2007 | Richards et al. |
| 2007/0250013 A1 | 10/2007 | Brennan et al. |
| 2009/0062741 A1 | 3/2009 | Smith et al. |

FOREIGN PATENT DOCUMENTS

| | | |
|---|---|---|
| FR | 2666986 A1 | 3/1992 |
| WO | WO-9813094 | 4/1998 |
| WO | WO-2007109915 A1 | 10/2007 |
| WO | WO-2007131371 A1 | 11/2007 |

OTHER PUBLICATIONS

International Search Report and Written Opinion mailed Feb. 18, 2010 for PCT/US009/062298 claiming benefit of U.S. Appl. No. 12/260,541, filed Oct. 29, 2008.

Notification Concerning Transmittal of International Preliminary Report on Patentability for PCT/US2009/062298 mailed May 12, 2011; 9 pages (2011).

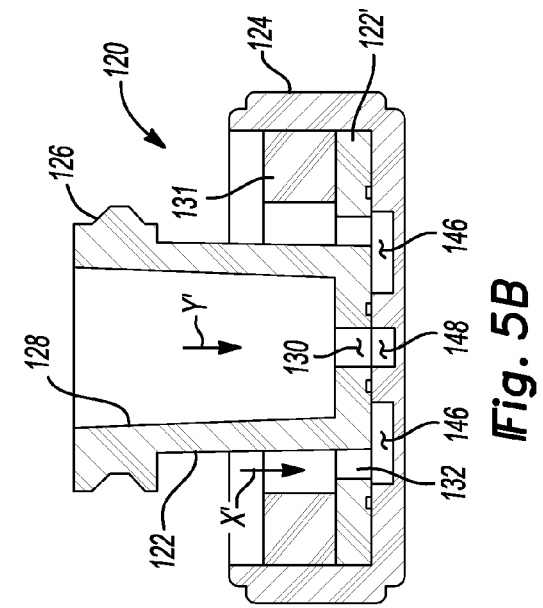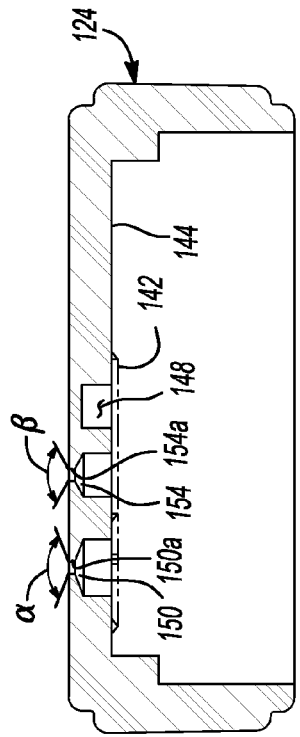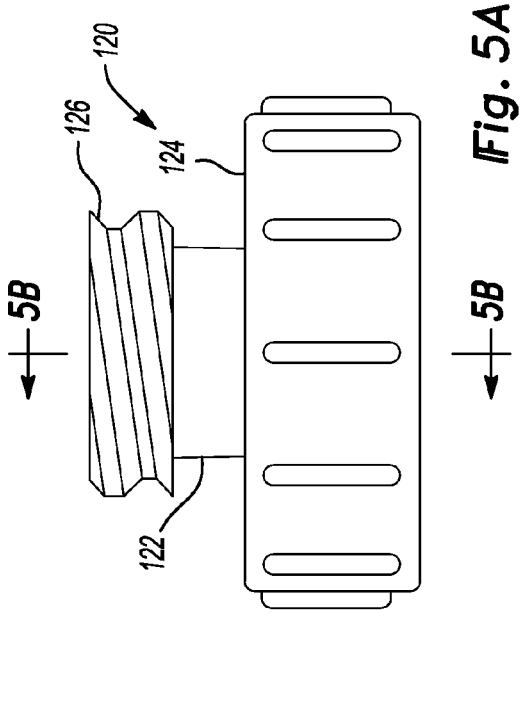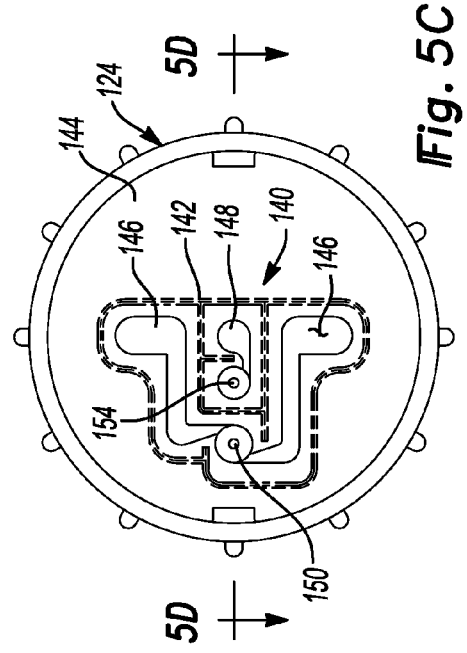

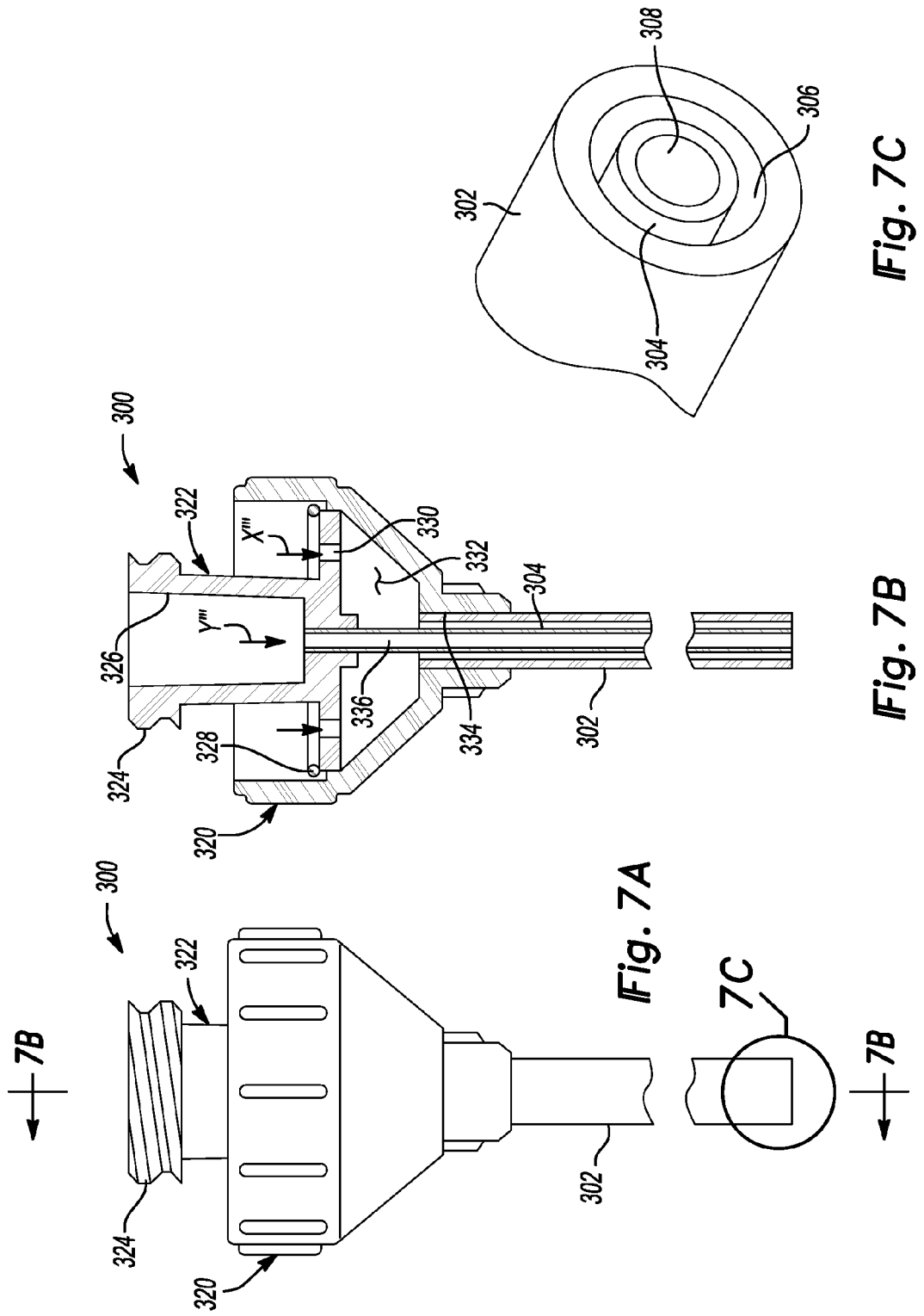

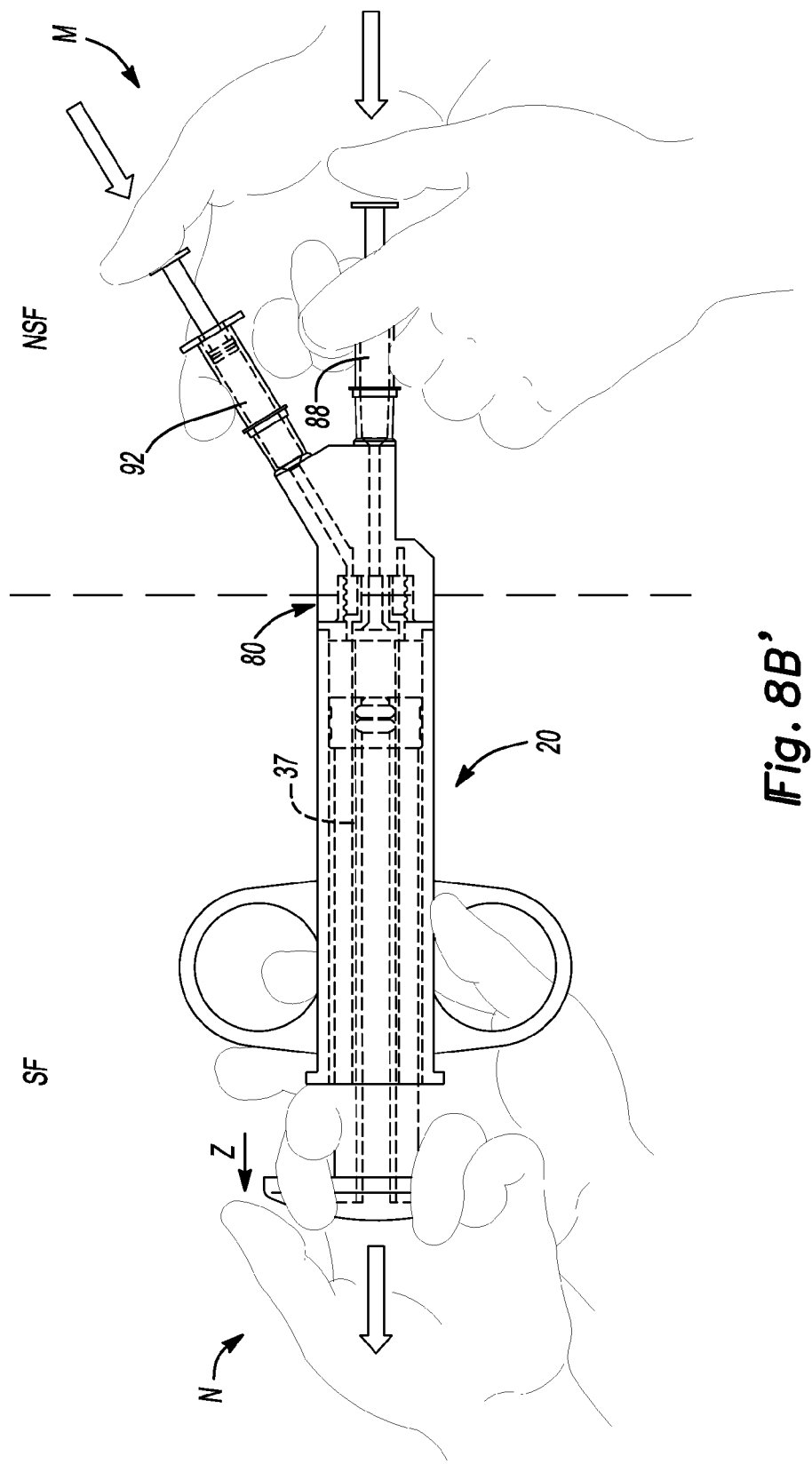

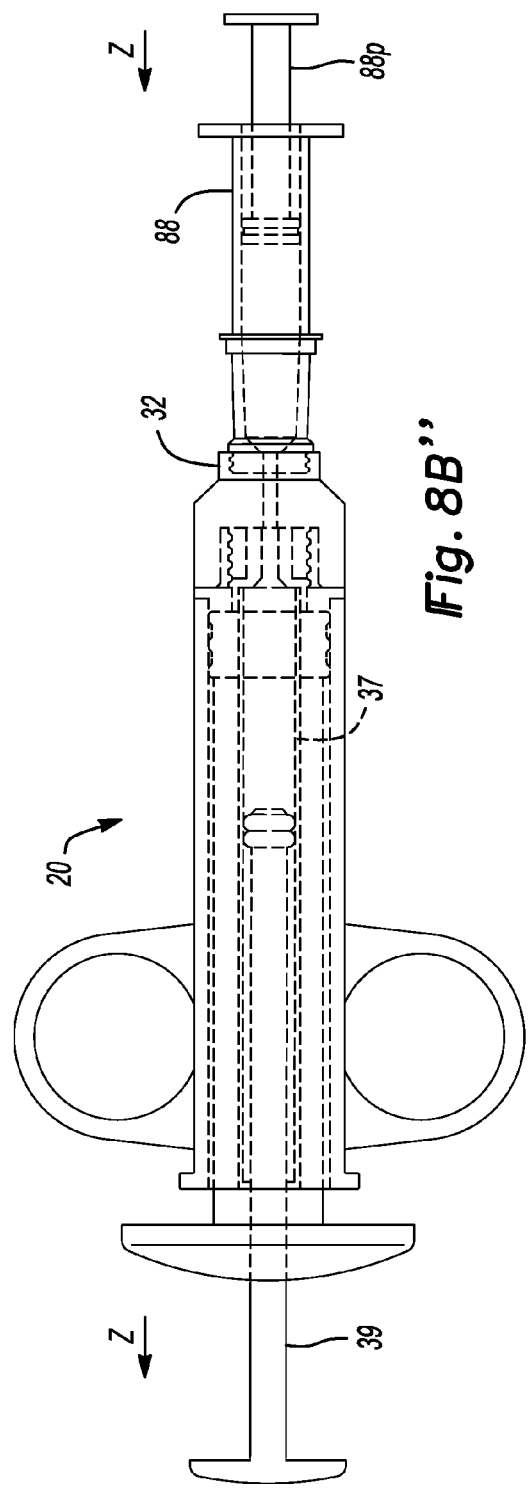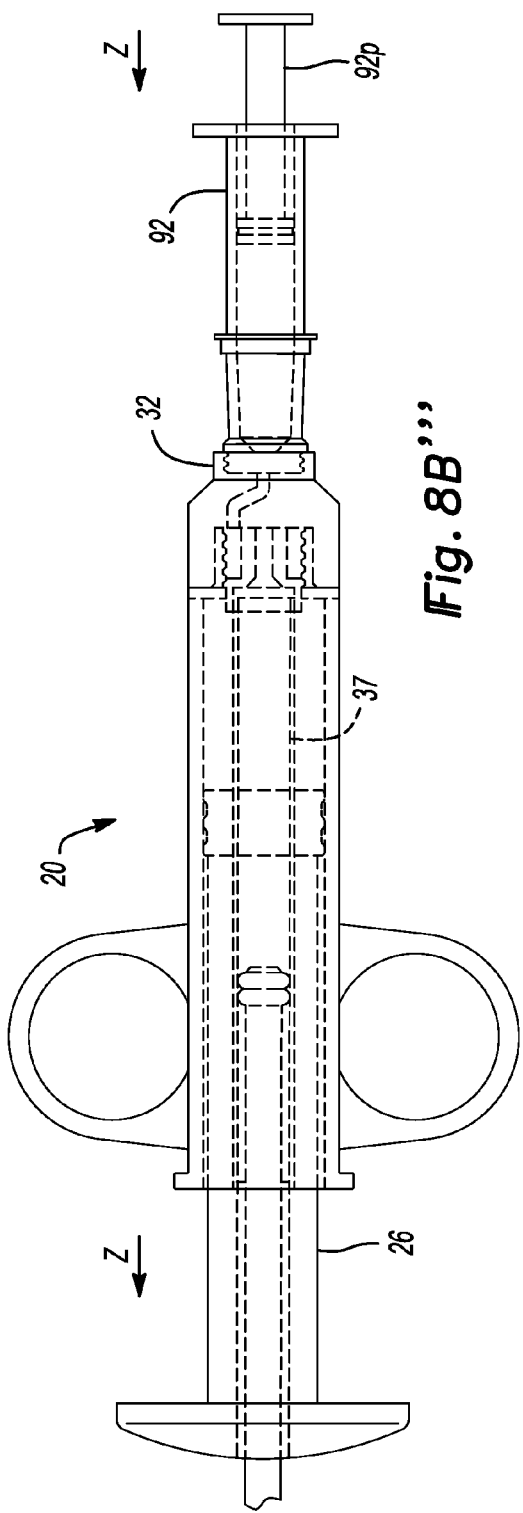

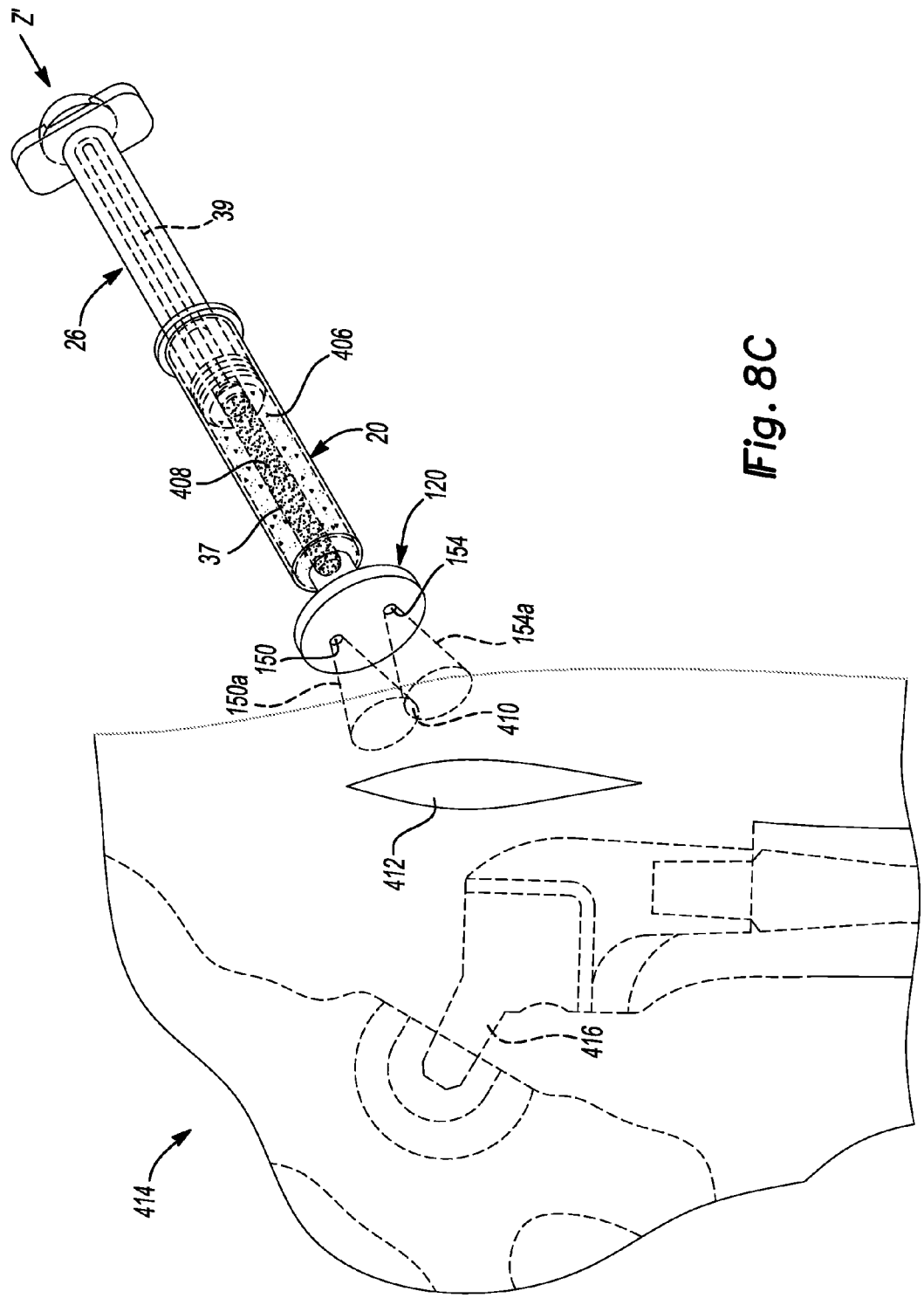

METHOD AND APPARATUS FOR CONTAINING, TRANSPORTING, AND PROVIDING A MATERIAL

CROSS-REFERENCE

This application is a divisional of U.S. patent application Ser. No. 12/260,541 now U.S. Pat. No. 8,523,805 filed on Oct. 29, 2008. The entire disclosure of the above application is incorporated herein by reference.

FIELD

The disclosure relates generally to providing a container system that holds and mixes a material for application, and particularly to a container that at least separately holds two materials and is operable to express them to be mixed at a selected location.

BACKGROUND

The statements in this section merely provide background information related to the present disclosure and may not constitute prior art.

During various procedures, two or more components can be combined to form a mixture of the materials for various purposes. For example, a first and second material may be mixed to polymerize, seal, or the like. For example, thrombin and fibrinogen can be mixed to form a tissue sealant that is biocompatible.

Autologous material can be used to form a tissue sealant. The tissue sealant materials, including thrombin, can be extracted or concentrated from a patient, such as from a whole blood sample. The tissue sealing materials can be provided or held separately until applied to an area to be sealed.

A tissue sealant can be used in various procedures, such as a minimally invasive procedure to speed healing. In addition, an autologous material can provide various benefits such as reducing or eliminating cross contamination or infection. The materials that can form a tissue sealant, however, are generally held separately until applied to a selected area.

SUMMARY

A device is disclosed that includes a first chamber or area and a second chamber or area to hold two materials that can be mixed at a selected time. The device can be used to selectively express one or both of the materials for mixing at a selected location. The device can include a coaxial syringe or expressing assembly that includes two plungers to express two materials from two separate chambers.

The device further includes mixing devices operable to mix selected materials during expression of the materials from the expressing assembly. Accordingly, the materials can be applied to an area, such as an area of a patient, under selected conditions. The mixing connections can include a spray of combined materials. Also, the materials can be expressed or sprayed in a manner that causes them to mix after expression, prior to expression, or during application to the patient. The materials can be mixed after or delivery through one or more tubes, as well.

Further, a process is disclosed for filling a selected container and expressing a material from a selected container. A dual chamber filling connection can be provided to allow for filling with at least two chambers of a single device with at least two materials. The two materials can be provided individually to the two chambers of the device.

According to various embodiments, a system to express at least two separated materials to a selected position is disclosed. The system can include a syringe assembly, including a first chamber and a second chamber operable to maintain a first material separated from a second material; an outlet portion including an outlet connection portion extending from a wall, a first passage defined by the wall extending from the first chamber, and a second passage extending from the second chamber; and a first plunger operable to move in the first chamber and a second plunger operable to move in the second chamber. The system can further include a tip portion operable to connect near the outlet portion. The tip portion can include a tip connection portion including an inner wall operable to be associated with the outlet connection portion; a first tip passage operable to be associated with the first passage when the tip portion is connected to the outlet portion; a second tip passage operable to be associated with the second passage; and a sealing member positioned between the tip portion and the outlet portion to assist in sealing the second tip passage to the outlet portion. The seal can be provided by mating or contacting taper walls, a separate sealing member, a sealant, or other appropriate mechanisms or materials. The association of the inner wall and the outlet connection portion is to assist in directing material from the first passage. The first material in the first chamber and the second material in the second chamber are operable to be expressed through the tip portion.

According to various embodiments, a tip portion operable to be connected to a syringe assembly, wherein the syringe assembly includes a first chamber separated from a second chamber and an outlet defining a first passage from the first chamber and a second passage from the second chamber is disclosed. The tip portion can include a tip connection portion including an inner wall operable to be associated with the outlet; a first tip passage operable to be associated with the first passage when the tip portion is connected to the outlet, wherein the association of the inner wall and the outlet is to assist in directing material from the first passage to the first tip passage; and a second tip passage operable to be associated with the second passage. The tip portion can further include a sealing member positioned between the tip connection portion and the outlet to assist in sealing the second tip passage to the outlet; an end housing portion operably connected to the tip connection portion; a member operably connected to the end housing portion; and a directing wall extending from the member. A first material in the first chamber and a second material in the second chamber are operable to be expressed through the tip portion.

According to various embodiments, a method of expressing a material to a selected site from a syringe assembly is disclosed. The method can include filling a first chamber of the syringe assembly with a first material and filling a second chamber of the syringe assembly with a second material. A first passage in the syringe assembly can be provided to extend from the first chamber and a second passage can be provided in the syringe assembly extending from the second chamber. A tip portion can be connected with the syringe assembly. Also, a directing wall can be formed or provided within or to extend from an interior surface of the tip portion and the first material and the second material can be directed. The materials can be directed with the directing wall.

According to various embodiments, a tip portion operable to be connected to a syringe assembly, wherein the syringe assembly includes a first chamber separated from a second chamber and an outlet defining a first passage from the first chamber and a second passage from the second chamber is disclosed. The tip portion can include a tip connection portion including an inner wall operable to be associated with the outlet; a first tip passage operable to be associated with the first passage when the tip portion is connected to the outlet, wherein the association of the inner wall and the outlet is to assist in directing material from the first passage to the first tip passage and a second tip passage operable to be associated with the second passage. The tip portion can further include a sealing member positioned between the tip connection portion and the outlet to assist in sealing the second tip passage to the outlet; an end housing portion operably connected to the tip connection portion; and a member operably connected to the end housing portion, Associated with the end housing portion, the member, or the tip connection portion can be a first tube member extending from said member associated with the first tip passage and a second tube member extending from the end housing portion a distance from the member associated with the second tip passage. The second tube is coaxial and extends around the first tube member. Also, a first material in the first chamber and a second material in the second chamber are operable to be expressed through the tip portion.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 5A is a side plan view of a tip portion, according to various embodiments;

FIG. 5B is a cross-sectional view of a tip portion, according to various embodiments;

FIG. 5C is an end housing of a tip portion, according to various embodiments;

FIG. 5D is a cross-sectional view of an end housing of a tip portion, according to various embodiments;

FIG. 7A is a plan view of a tip portion, according to various embodiments;

FIG. 7B is a cross-sectional view of FIG. 7A;

FIG. 7C is a detailed perspective view of an outlet portion of two tubes of a tip portion, according to various embodiments;

Figure 8A:
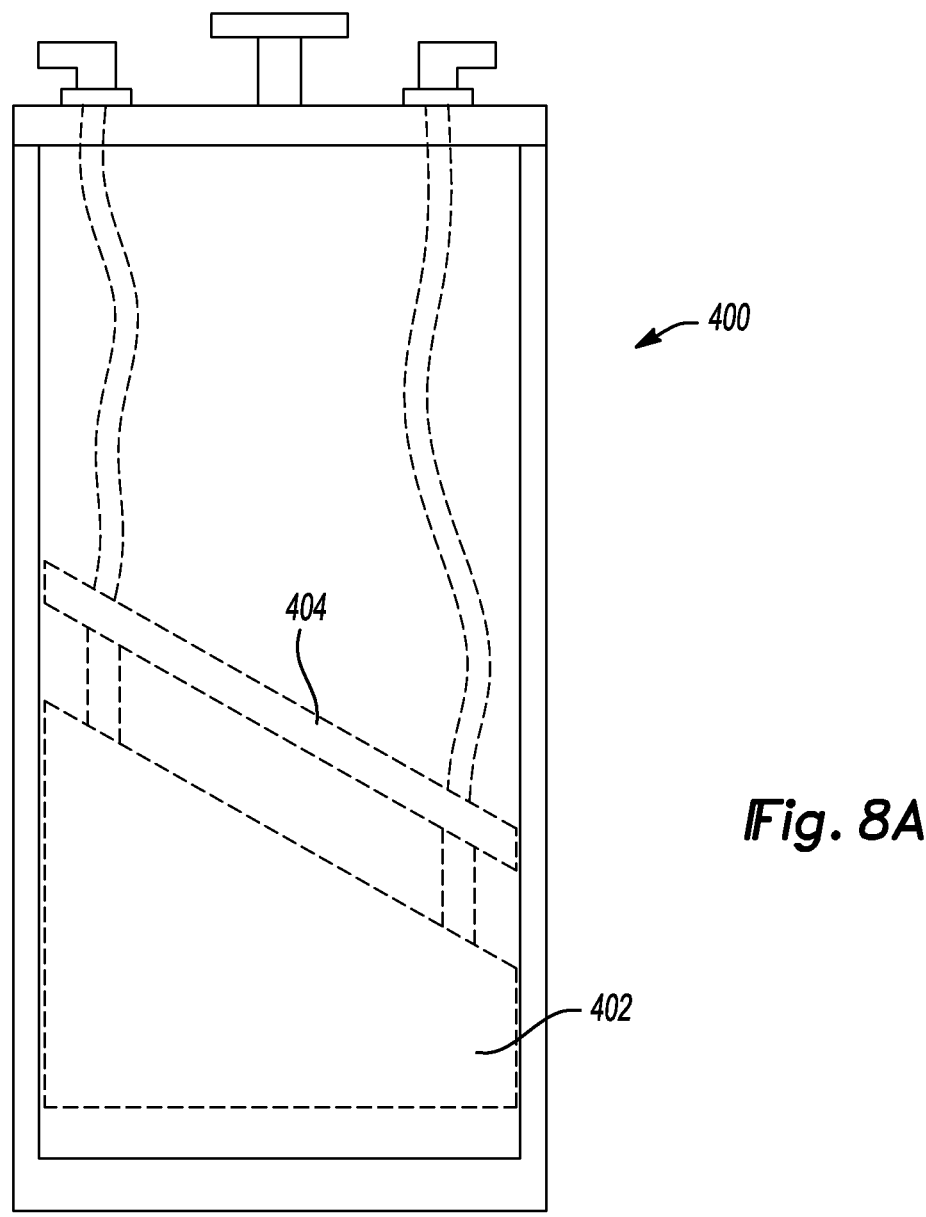
FIG. 8A is a separation assembly.
Figure 8B:
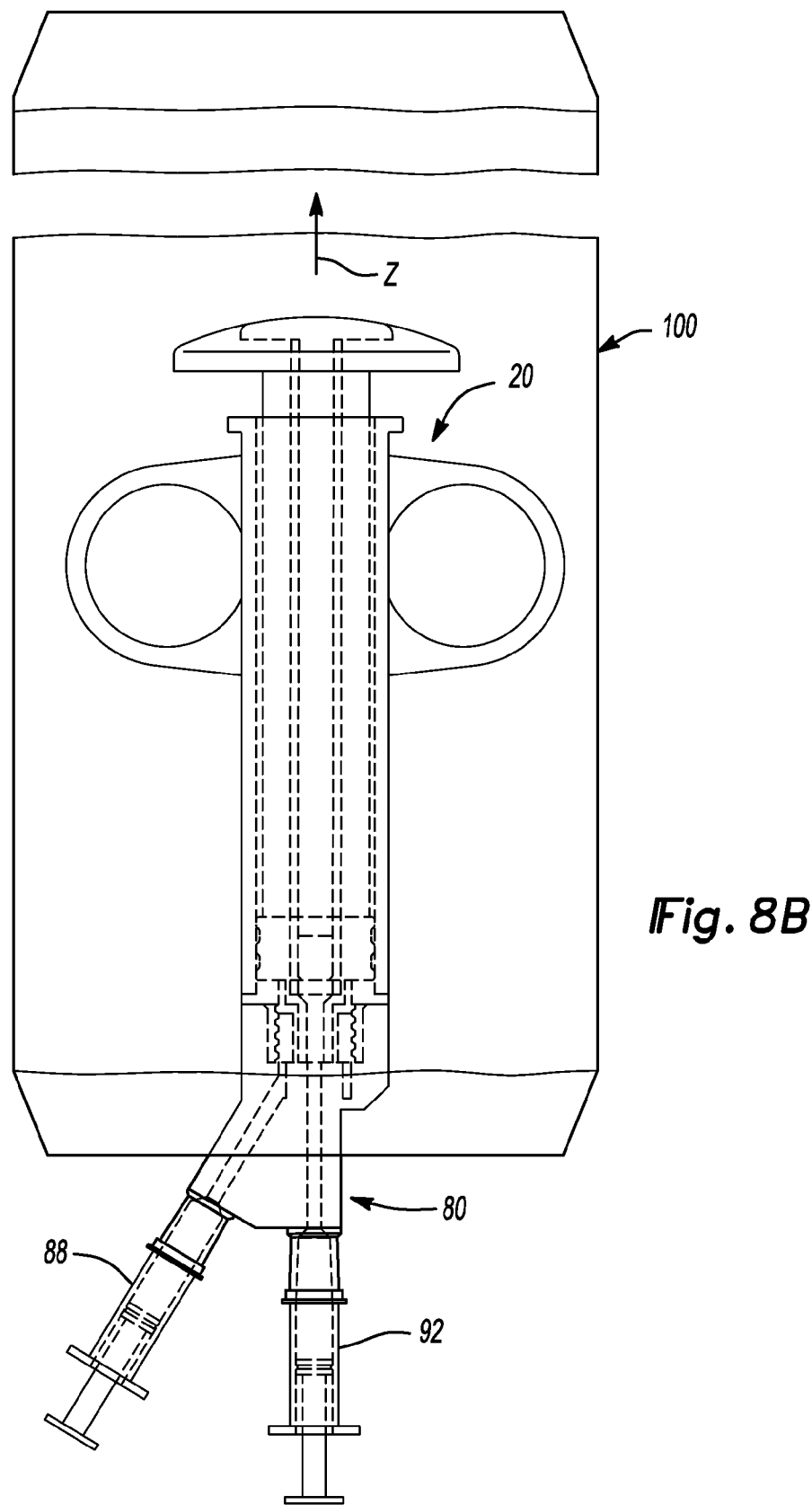
FIG. 8B is an expressing assembly operable to be filled within a sealing pouch, according to various embodiments.

FIG. 8B' is an environmental view of an expressing assembly being filled and delivered to a sterile field, according to various embodiments, and FIGS. 8B" and 8B'" are environmental views of an expressing assembly being filled from two containers, according to various embodiments, FIG. 8C is an environmental view of an expressing assembly expressing material onto a selected site, according to various embodiments.

DETAILED DESCRIPTION

The following description is merely exemplary in nature and is not intended to limit the present disclosure, application, or uses.

Figure 1A:
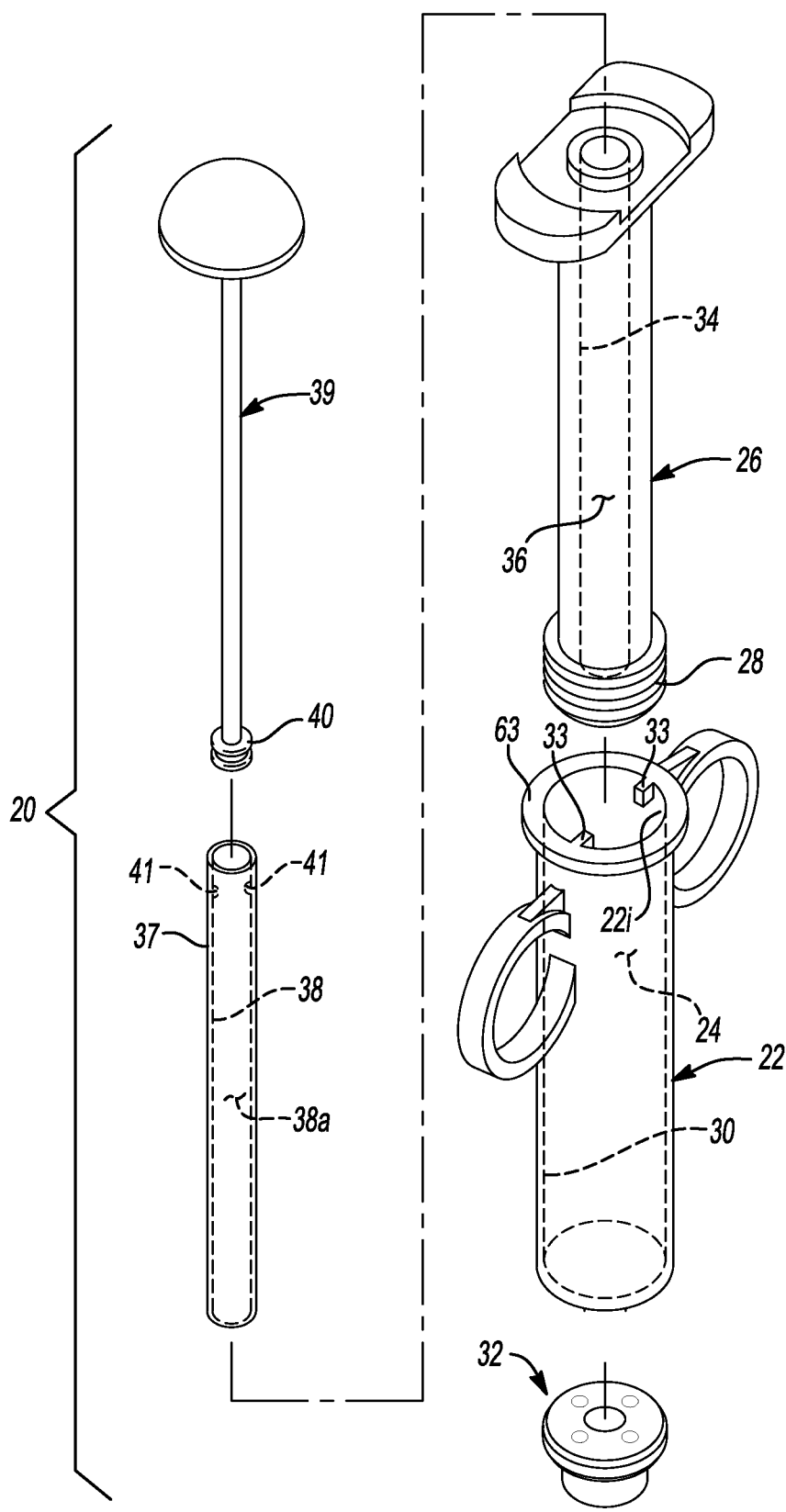
FIG. 1A is an exploded view of an expressing assembly, according to various embodiments.
Figure 1B:
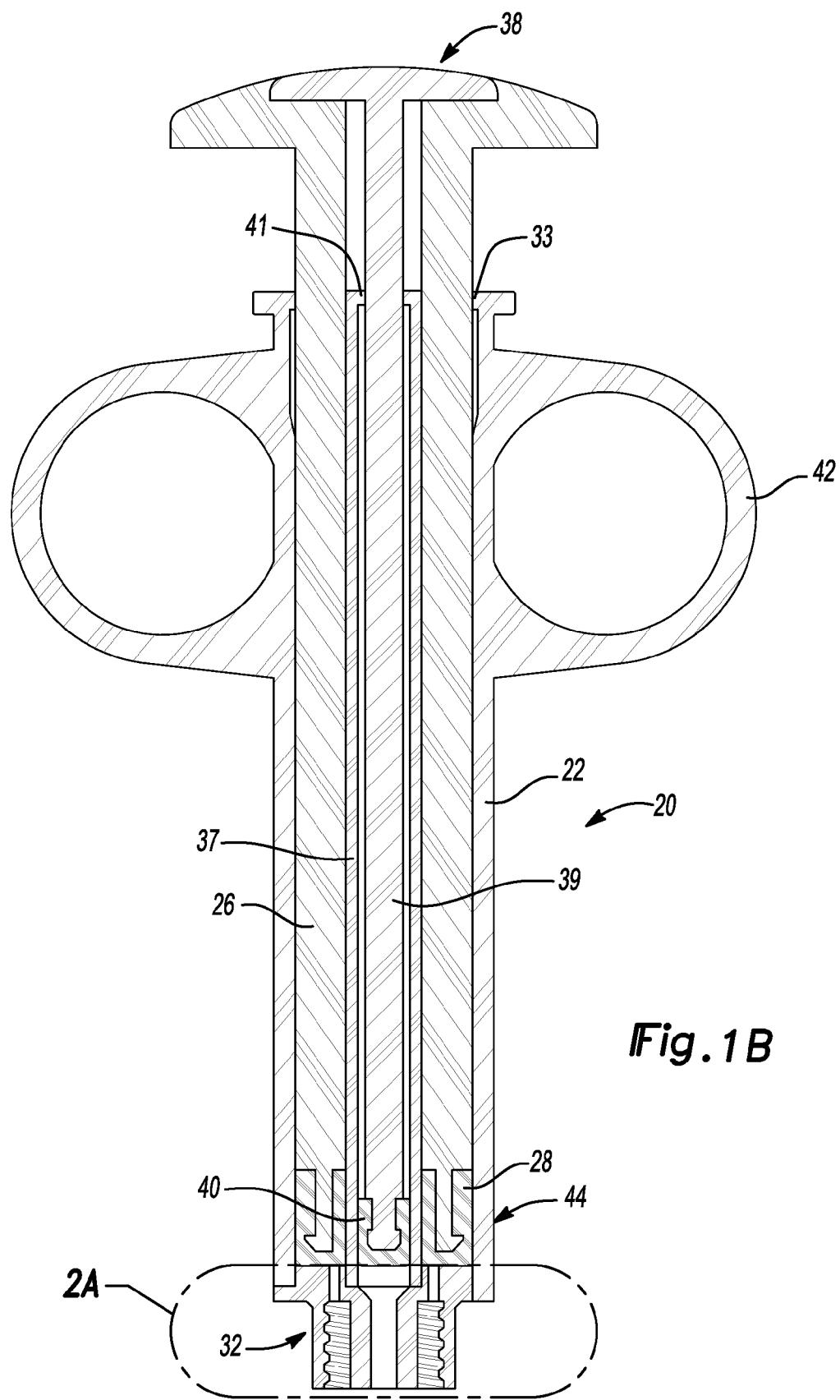
FIG. 1B is a cross-sectional view of an expressing assembly, according to various embodiments.

With reference to FIGS. 1A and 1B, an expressing assembly 20, also referred to as a syringe assembly, is illustrated. The expressing device 20 can generally include an external container or syringe housing 22 that defines or has an internal chamber 24. A first or outer plunger 26 is able to fit within the inner chamber or volume 24 of the external container 22 defined by an internal wall 30. The outer or first plunger 26 can include an outer plunger tip 28 operable to substantially mate with or wipe the internal wall 30 of the external container 22. In this way, the first plunger 26 is operable to move within the external container 22 to express a material through an outlet end 32 of the external container 22. One or more stop portions, such as projections or fingers 33, can extend from the internal wall to act as a stop for the plunger 26. The outer plunger tip 28 can have an external dimension greater than another portion of the plunger and engage the stops 33. As discussed herein, the material expressed with the first plunger 26 can be expressed through a selected pathway or passage 60a (FIG. 2B) through the outlet end 32. The outlet end 32 can be interconnected with the external container 22 in any appropriate manner such as molded or formed as one member, fixed together with adhesives, welding, solvent bonding, etc.

The first plunger 26 has an internal wall 34 that defines a cannula or passage 36 substantially through a length of the first plunger 26. A second chamber tube 37 is operable to be positioned within the passage 36 of the first plunger 26. The second tube 37 can be fixed relative to the outlet end 32 according to any appropriate mechanism, such as adhesives, molding, welding etc. For example, the tube 37 can be formed as a single member with the outlet end 32 or even with the external container 22.

The second chamber tube 37 can also include an inner wall 38 which defines an internal passage 38a. The internal passage 38a can be filled with a selected material, as discussed herein. Also, as discussed herein, the second chamber or inner tube 37 allows a second material to be placed within the passage 38a and kept separate from a separate area of the interior 24 of the external container 22 until expressed from the expressing device 20.

The external container 22, outlet end 32, and the inner tube 37 can be all formed together as one piece, for example molding them all as one piece. The external container 22, outlet end 32, and the inner tube 37 can also each be formed separately and connected together with adhesives, welding, solvent bonding, etc. Further, any two of the external container 22, outlet end 32, and the inner tube 37 can be formed together as one piece and then connected to the third, as discussed above.

The external container 22 and the internal tube 37 can both be of the same, similar, or different cross-sections. For example, both the external container 22 and the internal tube 37 can be cylinders that are positioned coaxially. It will be understood, however, that the two may be different cross-sections, such as the external container 22 being a cylinder and the internal tube 37 being hexagonal in cross-section.

A second or inner plunger 39 is operable to fit within the second passage 38a of the second tube 37. The second plunger 39 includes a second or inner plunger tip 40 that is able to substantially wipe the internal wall 38 of the second tube 37. As the second plunger 39 passes through the passage 38a of the second tube 37, the second material can be expressed through the outlet end 32 of the external container 22. A stop portion, such as one or more fingers or projections 41, can extend into the second passage 38a of the inner tube 37. The tip 40 of the plunger 39 can engage the projections 41 similar to the first plunger 26 engaging the projections 33 of the external container 22. Also, as discussed further herein, the material expressed with the second plunger 39 can take a selected pathway or passage 62 (FIG. 2B) through the outlet 32 that is different than the pathway taken by the first material expressed with the first plunger 26 through the outlet 32.

The first plunger 26 and the second plunger 39 can be operated individually or together. The material in the two chambers can be filled into the two chambers or expressed from the two chambers at the same or different times. In addition, the plungers 26, 39 being operated separately allows for selected and varying volumes of the two materials to be expressed.

A first area between the external container 22 and the internal tube 37 defines a first cross-section area. A second area defined by the passage 38a defines a second cross-section area. The first and the second cross-section areas can be the same or different in the expressing device 20. In addition, the cross-section areas can be selected to select the volume of the two materials positioned in the two separate areas. This can be used to select different expression rates or volumes of the two materials. Accordingly, a selected concentration or mixture of materials can be selected. For example, as discussed herein, a higher volume of fibrin can be expressed per unit of plasma or other material to form a faster setting or thicker material. Other mixtures can also be formed for selected purposes.

The external container 22 can further include various portions, such as finger grips 42. The finger grips 42 can include one or more finger grips 42 that are operable to be grasped with the hand of a user during expression or filling of the expressing device 20. The finger grips 42, for example, can be held with a first and second digit of a single hand while a thumb of the same hand of the user depresses the plungers 26, 38 to express a material out of the outlet 32.

Figure 2A:
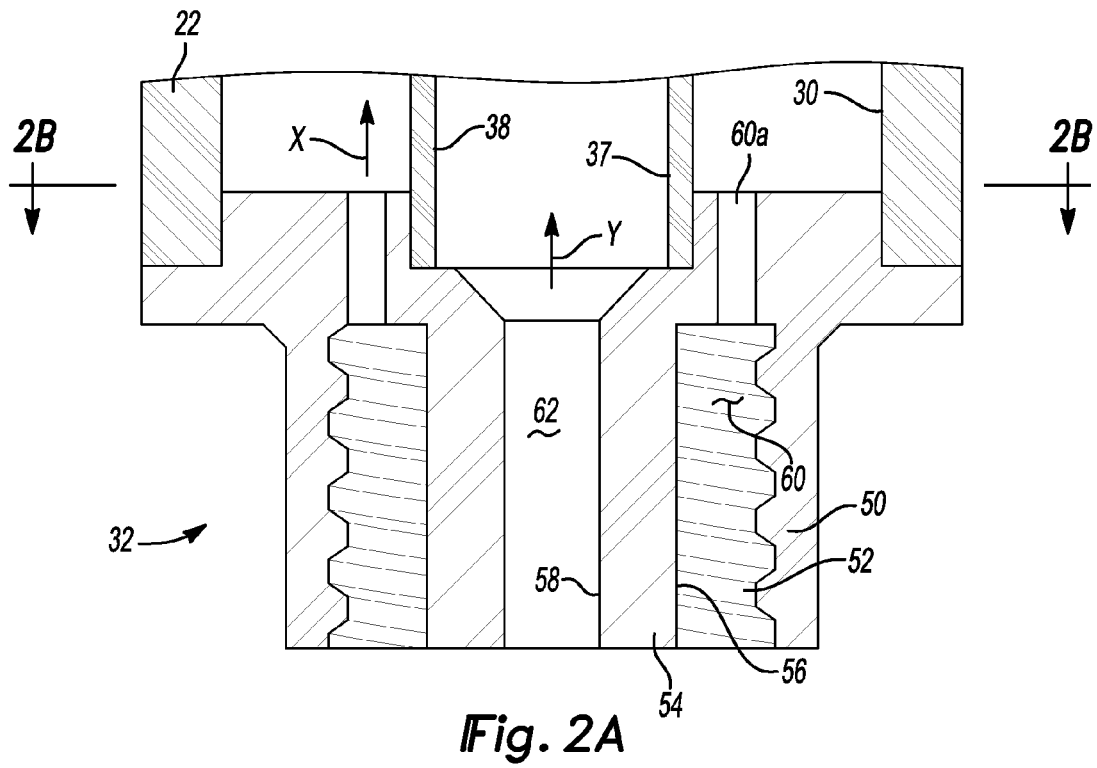
FIG. 2A is a detailed view of an outlet of an expressing assembly, according to various embodiments.
Figure 2B:
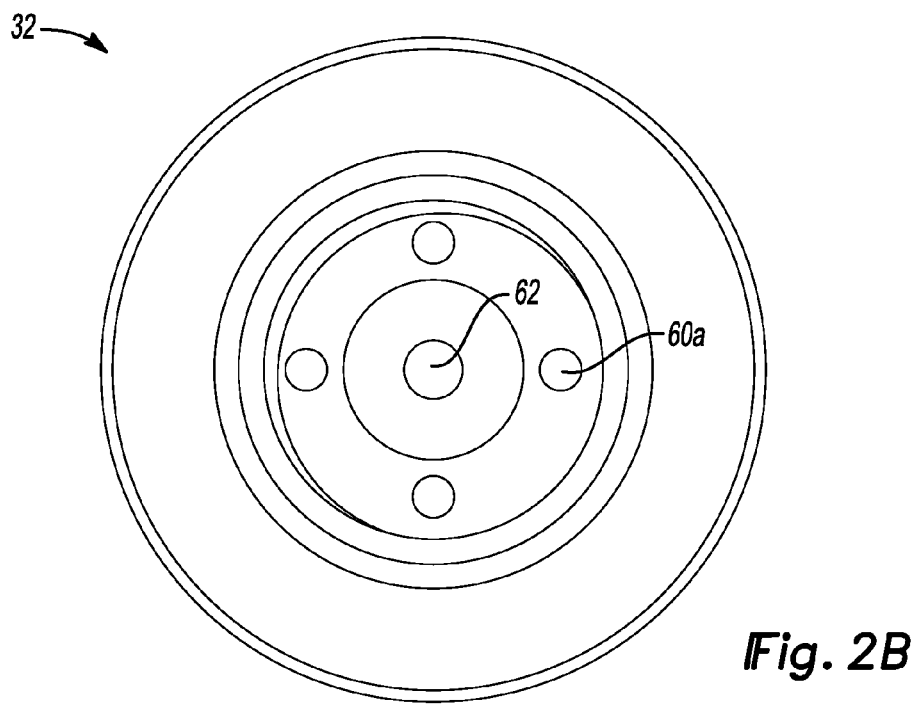
FIG. 2B is a top plan view of an outlet, according to various embodiments.
Figure 3A:
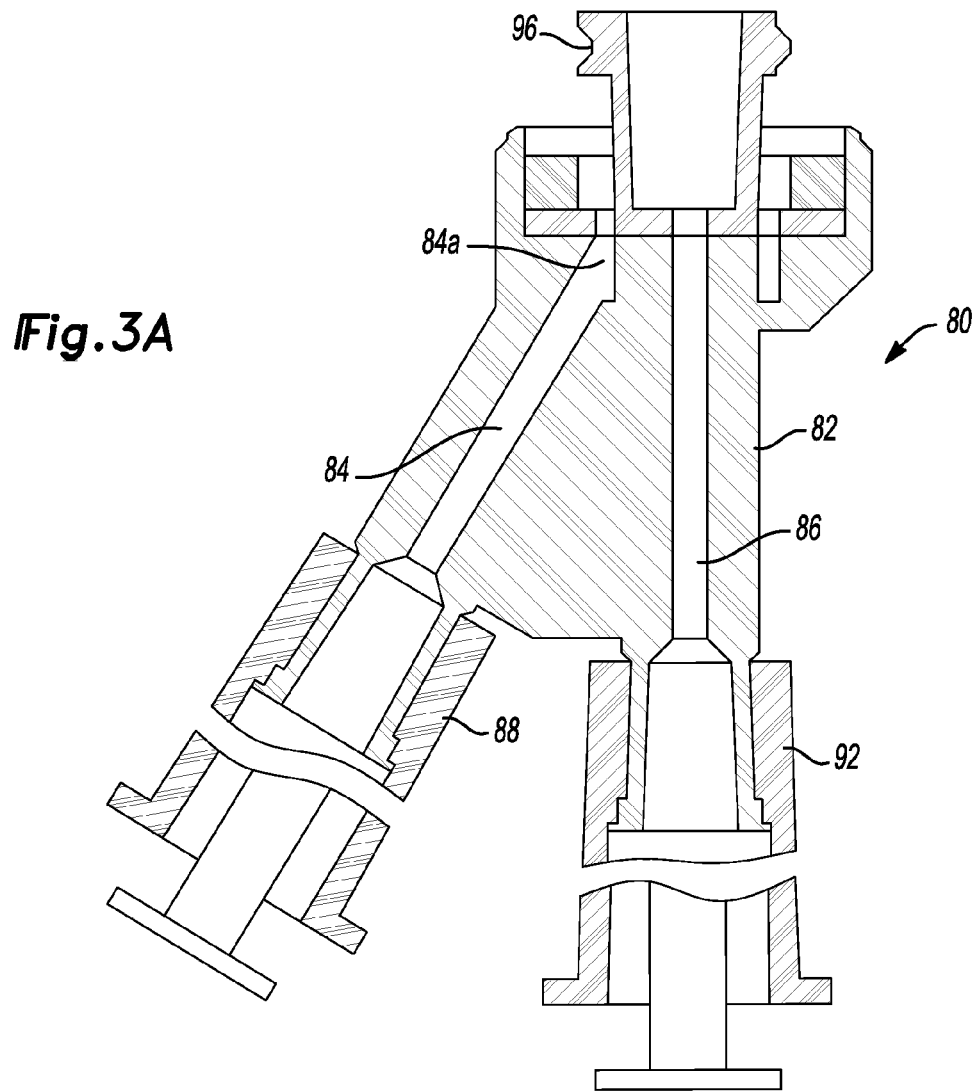
FIG. 3A is a tip portion or fill port, according to various embodiments.
Figure 3B:
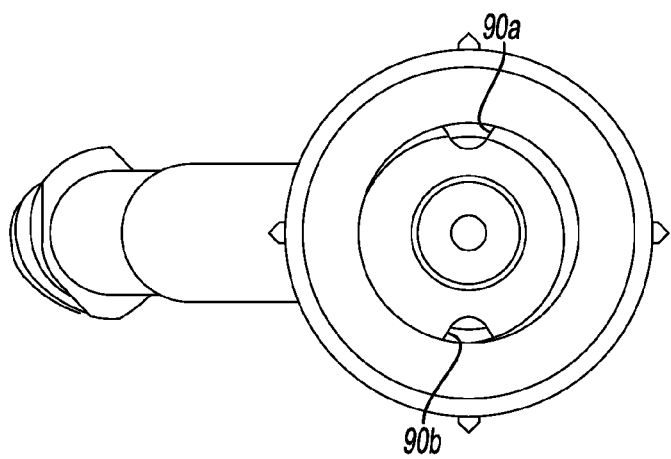
FIG. 3B is a top plan view of a tip portion or fill port, according to various embodiments.

With continuing reference to FIGS. 1A and 1B, and additional reference to FIGS. 2A and 2B, the outlet end 32 is illustrated in detail. The outlet end 32 can be formed integrally with the external container 22 or as a separate component that is mounted to an end 44 of the external container 22. The end 44 can be a distal or outlet end to which the outlet tip 32 is interconnected. Nevertheless, it will be understood that various molding techniques, such as injection molding or extrusion molding, can be used to mold the external container 22 as a single piece with the outlet tip 32.

The outlet tip 32 can include an external wall 50 that includes an interior portion defining an internal or inner diameter thread 52. The internal thread 52 can be a thread that is operable to engage a fitting or connection portion. The inner wall including the inner thread 52 can be positioned a spaced distance from a second internal wall 54. The second internal wall 54 can include an external surface 56 and an internal surface 58. Also, the external surface 56 can be configured, such as tapered or angled relative to the external container 22, for connection or sealing with a separate member.

Defined between the external surface 56 and the internal thread 52 can be a first passage or portion of the first passage 60. The first passage 60 can be defined through any appropriate portion of the outlet tip 32 and can further include a second passage portion 60a. A plurality of the second passage portions 60a can be associated with the first passage 60. As illustrated in FIGS. 1A-2B, one or more of the second passage portions 60a can be provided that in communication with the first chamber defined by the external container 22 and the first passage portion 60. The plurality of second passage portions 60a can be positioned around the outlet portion 32 and second passage 62.

The second passage portion 60a can allow for passage of a material into a first portion or chamber of the external container 22. As discussed further herein, the first material can pass through the first passage 60, 60a (generally in an upstream direction) to fill the first chamber and later be expressed with the first plunger 26 in a reverse direction (generally downstream) through the first passage 60, 60a in a selected manner.

The internal wall 58 defines a second passage 62 that allows a second material to be placed into a second chamber defined by the inner tube 37. The second passage 62 can be concentric with an annular ring defined by the first passage 60 or at any appropriate location. Also, as discussed further herein, the second material can be expressed in a reverse direction (generally downstream) through the second passage 62 with the second plunger 39. Accordingly, as discussed herein, two materials can be placed into the external container 22 at a first time and be expressed from the external container 22 at a second time. As discussed above briefly, the materials can be positioned in the external container 22 for later expression and mixing to form selected materials, such as a tissue sealant.

Two separate materials can be provided individually to the expressing assembly 20. With continuing reference to FIGS. 2A and 2B and returning reference to FIGS. 1A and 1B, the materials can be provided through the passages generally in a downstream (during expression of a material) direction of arrow X through passage 60A and arrow Y through passage 62. For example, a first material, including those discussed herein, can be moved through the passage 60a into an area between an exterior wall of the internal tube 37 and the internal wall 30 of the external container 22. Because of the internal tube 37, the first material that is moved through passage 60a generally in the direction of arrow X will stay separated from any material positioned within the internal tube 37. The material can be moved through the passage 60a in any appropriate manner and with any appropriate mechanisms or devices, including those discussed herein. In addition, a second material can be moved through the second passage 62 generally in the direction of arrow Y into the internal tube 37. The internal wall 38 of the internal tube 37 maintains a second material separated from the first material that is positioned between the inner tube 37 and the inner wall 30 of the external container 22. It will be understood that the first and second materials can be provided through the passages at a single time, using an appropriate delivery mechanisms, or at substantially separate times. Accordingly, the outlet end 32 can also be an inlet for filling the expressing assembly 20. It will be understood, however, that the expressing assembly 20 can also be filled from a plunging or open end 63 (FIG. 1A). The expressing assembly 20 can be filled once the inner tube 37 is positioned within the external housing 22 to define the two distinct areas within the expressing assembly 20. Accordingly, the expressing assembly 20 can be filled from either end in an appropriate manner, but the inner tube 37 can maintain the second material from being mixed or combined with the first material within the expressing assembly 20.

With additional reference to FIGS. 3, 3A, 3B and 4, a filling portal 80 is illustrated. The filling portal 80 can also be referred to as a tip portion operable to be attached to the external container 22. The portal 80 includes an outer housing 82 that includes or defines a first passage 84 and a second passage 86. The two passages 84, 86 are operable to allow materials to move from a first supply container 88 through the first passage 84 and through the first passage 60a of the expressing assembly 20. The first passage 60a of the expressing assembly 20 can be substantially aligned with a first passage extension portion 84a of the port 80. It will be understood that any appropriate number of the passage extension portions 84a can be provided. Additionally, any appropriate number of the first passage portion 60a can be provided. For example, four discreet passages can be provided and substantially aligned when the expressing assembly 20 is connected with the port 80. Alternatively, or in addition thereto, a substantially annular ring can be provided as the passage extension portion 84a and the first passage portion 60a of the expressing assembly 20. It will be understood that any appropriate design, diameter, or the like can be provided for the first passage 60a of the expressing assembly 20 and the first passage extension portion 84a of the port 80.

The port 80 can be interconnected with the external container 22 by providing an external or outer threaded portion 96. Other exemplary connection systems include the LUER-LOK® hypodermic needle connecting system or variations thereof. The external threaded portion 96 can interconnect with the internal threaded portion 52 of the outlet region 32 of the expressing assembly 20. By selectively interconnecting the external threaded portion 96 with the outlet portion 32, the first passage extension portions 84a can be aligned with the first passage portion 60a of the expressing assembly 20. In addition, the external threads 96 cooperating with the internal threads 52 can allow for a disconnection of the expressing assembly 20 from the port 80. In addition, detents or passages 90a and 90b in the locking portion 96 can allow a material to move from the first port passage 84 to the first passage 60a of the expressing assembly 20. The detents 90a and 90b can be any appropriate geometry, for example semi-circle, square, or flat.

The detents 90a and 90b, according to various embodiments, are provided to allow material to pass out of the container 44 and pass the connection threads 126. It will be understood, however, that detents 90a and 90b are not necessary. Other mechanisms or systems can be provided. For example, the threads 52 and the connection portion 126 can be provided with an appropriate dimensions to allow the material to flow between them to exit through the tip portion, according to various embodiments.

The port 80 also defines a second passage 86 that can allow for a material from a second supply source 92 to pass through the passage 86 and through the second passage portion 62 of the outlet portion 32. The second passage 86 in the port 80 can be aligned with the second passage 62 of the outlet portion 32 by interconnecting the threads 96 of the port 80 with the threads 52 of the outlet portion 32. The shape, size, or other characteristics of the second passage 86 and the second passage 62 of the outlet portion 32 can be provided in any appropriate and complimentary manner.

The first port passage 84 and the second port passage 86 allow for two materials, such as two separate and distinct materials from two sources 88, 92, to be positioned or passed through the two outlet passages 60a, 62 into the expressing assembly 20. The two materials can be provided separately or at separate times into the expressing assembly 20. As discussed further herein, the materials can be provided to the expressing assembly 20 and held within the expressing assembly 20 for appropriate purposes until selected to be expressed from the expressing assembly 20 together or separately.

Figure 4:
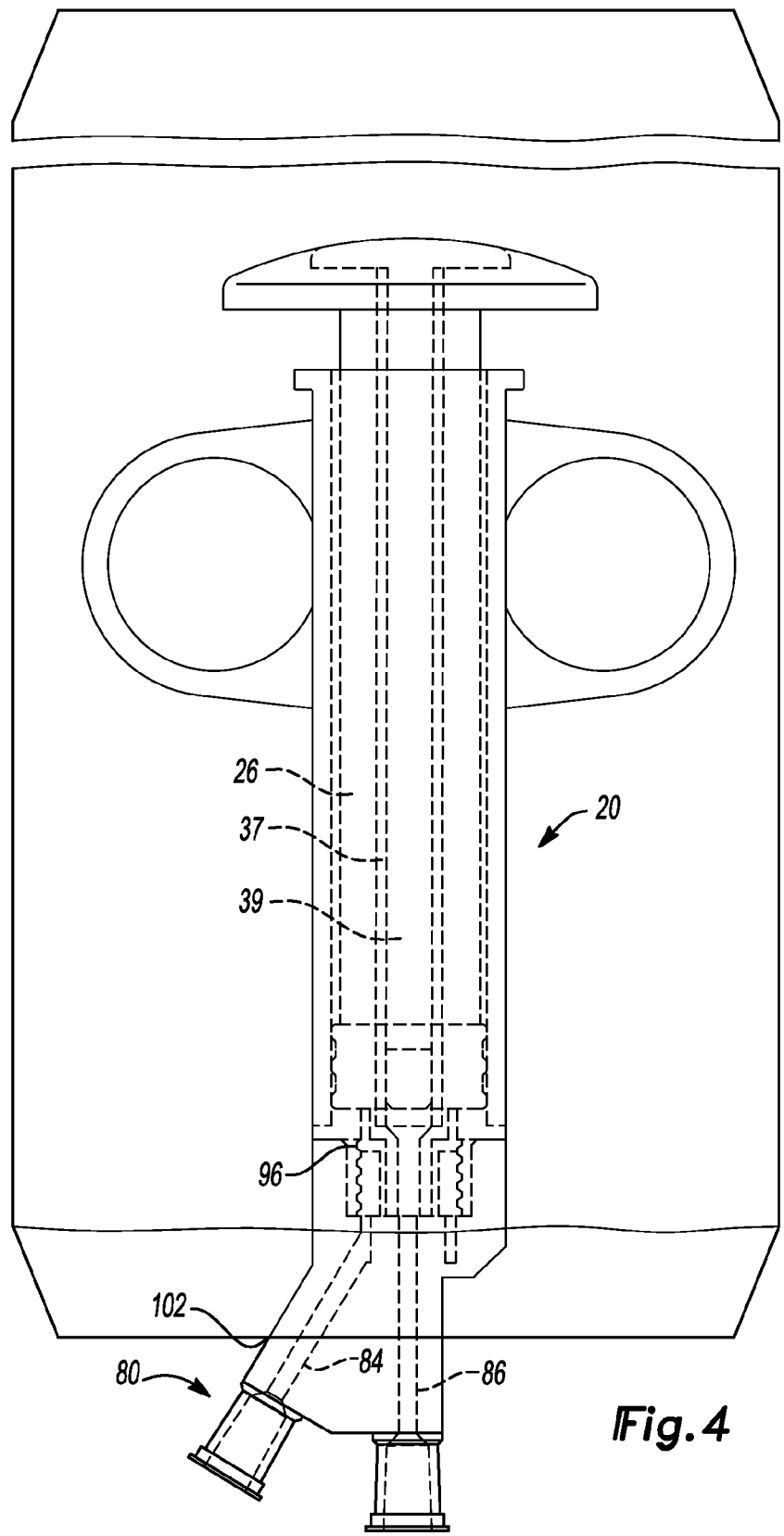
FIG. 4 is a view of an expressing assembly within a container.

Accordingly to various embodiments, the expressing assembly 20 can be provided within a sealed container 100, as illustrated in FIG. 4. The sealed container 100 can include a flexible package, such as a flexible bag, so that the expressing assembly 20 can be manipulated and operated from within the sealed package 100. The sealed package 100, however, can allow for sterilization of the expressing assembly 20 after positioning the expressing assembly 20 within the package 100. For example, portals maybe provided, such as one way valves, for introduction of a sterilization gas. In addition, various radiation, such as gamma irradiation, can be used to radiate the package 100 and the expressing assembly 20 to sterilize both the package 100 and the expressing assembly 20. The positioning of the expressing assembly 20 within the package 100, however, allows for introduction of material into the expressing assembly 20 via the port 80 while maintaining the expressing assembly 20 in the sterile environment provided by the package 100.

The port 80 can be provided in a sealed manner relative to the package 100. For example, the package 100 can be molded onto, around, or as a single piece with a portion of the port 80 such as at a sealing liner 102. The package 100 can also be interconnected with the port 80 with adhesives, welding, solvent bonding, or other appropriate techniques or materials. By sealing the package 100 around the port 80, the port 80 can be used to introduce two separate and distinct materials into the expressing assembly 20, as discussed above, while maintaining the expressing assembly 20 within the sterile environment provided by the package 100.

As an exemplary use, the expressing assembly 20 can be provided during an operative procedure for introducing materials into the expressing assembly 20. The package 100, including the expressing assembly 20 and the port 80 connected therewith, can be provided to a user in an operating theatre. After opening an external package and exposing the package 100, the expressing assembly 20 can be passed to a sterile field. Two materials can, therefore, be introduced into the expressing assembly 20 through the port 80 due to the ability to operate the expressing assembly 20 while it is contained within the package 100.

For example, a portion of autologous blood can be separated in an appropriate manner to concentrate or extract selected materials. Thrombin and fibrinogen can be introduced through the two separate passages 84, 86 in the port 80 to be placed in the expressing assembly 20 substantially separately. Containers and systems used to acquire the thrombin and fibrinogen, however, may be positioned in a substantially non-sterile environment. Using the expressing assembly 20 positioned within the package 100, however, the materials can be transferred to the expressing assembly 20 while it is maintained within the package 100 through the port 80, as illustrated in FIG. 8B. The expressing assembly 20 filled with the two materials, can then be transported to an operating theatre and transferred from a non-sterile area to a sterile area. Various sterile transfer techniques include those disclosed in Atkinson, Lucy Jo. *Berry & Kohn's Operating Room Technique, Seventh Ed.* Mosby-Year Book, Inc. 122-124. 1992.

It will be understood, however, that the expressing assembly 20 within the package 100 can be filled in any appropriate area, sterile or non-sterile or within an operating area or not and transported to any appropriate area such as a sterile or non-sterile area whether or not it is in an operating theatre. Accordingly, the expressing assembly 20 in the package 100 can be provided for appropriate purposes, such as maintaining a sterility or cleanliness of the expressing assembly 20 while it is within the container 100 but also while allowing operation of the expressing assembly 20 while it is within the container 100.

With reference to FIGS. 5A-5D, a first syringe attachment or tip portion 120 is illustrated. The tip portion 120 can include two main portions including a connection portion 122 and a directing or end housing portion 124. The connection portion 122 can include a thread or other appropriate lock or connection portion 126 to engage the threads 52 of the outlet end 32. The tip portion 120 can be interconnected with the expressing assembly 20 once a material has been provided into the expressing assembly 20.

At a selected time, such as after the expressing assembly 20 has been passed to a selected field, the tip portion 120 can be interconnected with the outlet region 32 of the expressing assembly 20. The tip portion 120 can be provided for various purposes, as discussed in detail further herein, such a spraying the materials positioned within the expressing assembly 20 through the tip portion 120. The tip portion 120 can allow a selected expression of the materials from within the expressing assembly 20.

The tip portion 120 including the end housing portion 124 and the connection portion 122 can be formed as a single member or interconnected at any appropriate time. For example, the tip portion 120 can be molded as a single piece within an appropriate molding technique, such as injection molding, blow molding, or any other appropriate procedure. Alternatively, however, the connection portion 122 can be interconnected with the end housing portion 120 such as with welding, adhesives, solvent bonding, or the like.

The connection portion 122 includes an interior wall 128 that can be positioned relative to the external wall 56 of the outlet portion 32 of the expressing assembly 20. The internal wall 128 of the connection portion 122 allows material passing through the second syringe passage 62 to pass through a first tip passage 130. A sealing member 131 can be provided to seal or assist in sealing the various passages. The sealing member 131 can be positioned against a plate 122' extending from the connection portion 122. Material passing through the first tip passage 130 generally pass in the direction of arrow Y', (generally downstream during expression) which is generally opposite of the direction to arrow Y.

Once the tip portion 120 is interconnected with the outlet portion 32 of the expressing assembly 20, the first passages 60a can be positioned substantially coaxially with the second passages 132 of the tip portion 120. Again, as material is expressed from the expressing assembly 20 it can generally move in the direction of X', which can generally be in the direction opposite to arrow X. The locking portion 126 can also include detents, like the detents 90a and 90b of the port 80, to allow material to move from the first syringe passage 60a to the second tip passage 132. Although, as discussed above, the detents 90a and 90b are not necessary and other provisions can allow material to move through the port 80.

Accordingly, the tip portion 120 can allow for positioning of the first tip passage 130 relative to the second syringe passage 62 of the syringe and a second tip passage 132 relative to the first syringe passage 60a of the expressing assembly 20. By positioning the two tip passages, 130, 132 of the tip portion 120 relative to the syringe passages 60a, 62 of the expressing assembly 20, material can be expressed through the tip passages 130, 132 to engage the end housing portion 124 of the tip portion 120.

The end housing portion 124 can include a material directing portion, surface, or wall 140. The material directing portion 140 can include a first directing region 146 and a second directing region 148 to collect and direct material from the expressing assembly 20. The first directing region 146 can be defined by a valley in a surface 144 of the end housing portion 124. The directing region may also or alternatively be defined by a small raised directing wall 142 (shown in phantom) that extends from a surface 144 of the end housing portion 124. The surface 144 can be provided to engage a surface of the outlet 32 or a portion of the connecting portion 122. When the surface engages near the outlet 32, as illustrated in FIG. 5B, the directing regions 146, 148 can define sealed or enclosed areas. The wall 142 can also be provided to be fused to the plate 122' extending from the connecting portion 122.

The first directing region 146 of the directing portion 140 can be positioned to receive material from the second tip passages 132 of the tip portion 120. The two tip passages 132 can direct material to the first directing region 146 defined in the end housing portion 124. The first directing region 146 can direct material to a first outlet passage or port 150. The first outlet port 150 can include an angled expression wall that is operable to direct a spray of material in an angle α. The angle α can be about 45° to about 170°. The angle α can be selected based upon the material to be expressed through the port 150 or for other appropriate purposes, such as increasing atomization of the material as it exits or is expressed from the tip portion 120. The material can be passed through the first directing region 146 to the outlet port 150 when the plunger 26 is depressed to express a material through the outlet portion 32.

The second directing region 148 can be provided to align relative to the first passage 130 in the tip portion 120. The second directing region 148 can direct material to a second outlet port 154 so that material can be expressed out the second outlet port 154. The outlet port 154 can have an expression wall angle β of about 45° to about 170°. The angle β can be selected for various purposes, including those for directing a material in a selected direction, such as mixing with a material being expressed through the first outlet port 150. Accordingly, the angles α and β can be provided to allow an overlap or form an overlap of materials expressed through the relative expression ports 150, 154.

The first and second directing regions 146, 148 can be provided as depressions within the external wall and below the surface 144 of the end housing portion 124 to assist in directing material to a selected outlet portion, such as the respective expression ports 150, 154 for expressing material through the ports to allow for a selecting mixing or positioned expression. Accordingly, it will be understood that the collection passages 146, 148 can be provided within the directing portion 140 in any appropriate manner or position. Additionally, the directing regions 146, 148 can be formed below the surface 144 in any appropriate manner. For example, machining, chemical etching, electrical etching, welding, molding, or the like can be provided to form the depressions and directing passages below the surface 144 of the end housing portion 124.

With reference to FIGS. 6A-6F, a tip portion or spray portion 200, according to various embodiments, is illustrated. The spray portion 200 can include an end housing portion 202 and a connection portion 204 substantially similar to the spray portion 120 discussed above. Therefore, these portions will not be discussed in detail here, it will only be discussed briefly. The connection portion 204 can include an external thread or appropriate lock or connection portion 206 to engage the outlet end 32 and can include an internal wall 208 to engage the external wall portion 54 of the outlet end 32 of the expressing assembly 20.

When the connection portion 206 engages the threadportion 52 of the outlet 32, a distal or end wall of the external container 22 can engage a sealing member 210 to seal the first chamber of the expressing assembly 20 with a first passage 212 of the tip portion 200. As discussed above, the internal wall 208 of the connection portion 204 can engage the external wall 56 of the outlet end 32 to provide a seal between the second chamber defined by the inner tube 37 and the second passage 214 of the tip portion 200. As discussed above, material can move generally in the direction of arrows Y' and X' through the passages 212, 214 to be expressed through the tip portion 200.

Figure 6A:
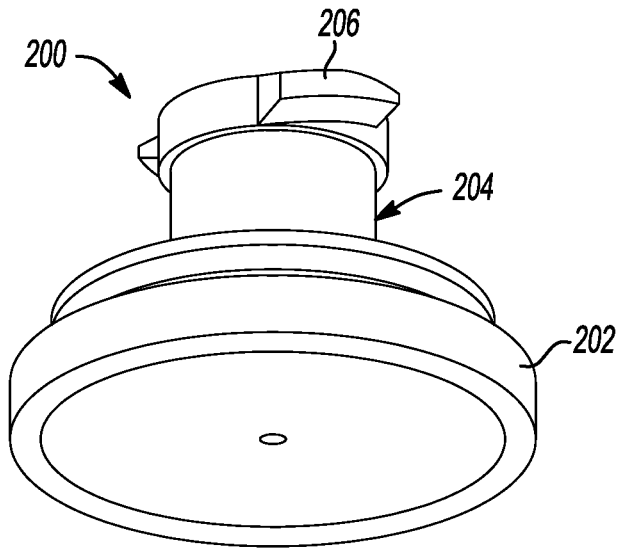
FIG. 6A is a bottom perspective view of a tip portion, according to various embodiments.
Figure 6B:
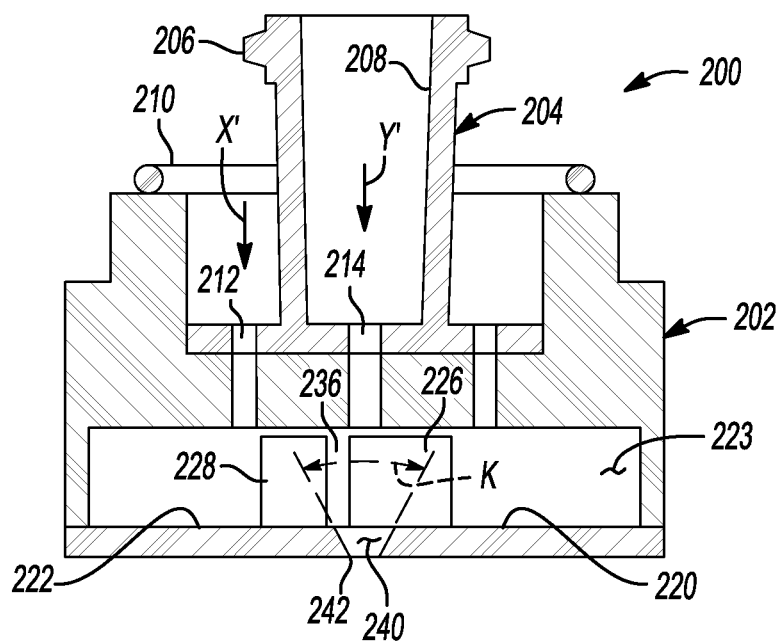
FIG. 6B is a cross-sectional view of a tip portion, according to various embodiments.
Figure 6C:
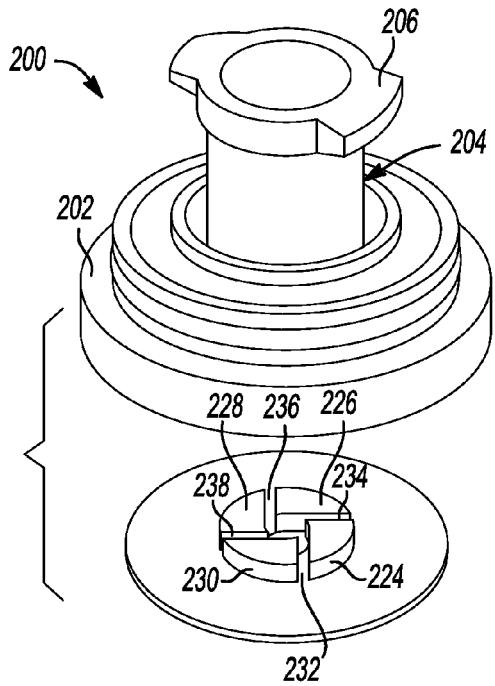
FIG. 6C is an exploded perspective view of a tip portion, according to various embodiments.
Figure 6D:
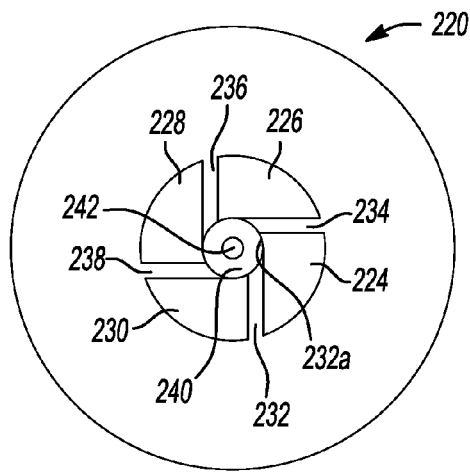
FIGS. 6D-6F are mixing surfaces of a tip portion, according to various embodiments.
Figure 6E:
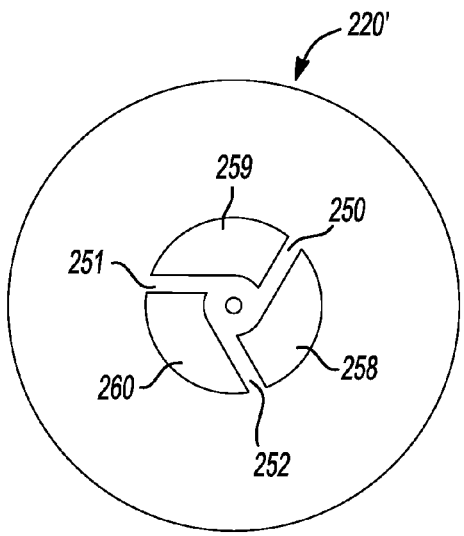

With continuing reference to FIGS. 6A and 6B and additional reference to FIGS. 6C and 6D, a mixing plate 220 can be interconnected with the end housing portion 202 of the tip portion 200. The mixing plate 220 can include a mixing surface 222 from which a plurality of directing wall sections 224-230 extend. Each of the wall portions 224-230 can define a plurality of channels 232-238 through which material can pass. The material can pass through the channel 232-238 to reach an expression sump 240 and finally an expression port 242. The expression sump can include or define an angle κ generally between about 45° and about 170°. The angle κ of the sump portion 240 can assist in creating a confluence or agitation of the materials expressed into the mixing area 223 defined by the mixing plate 220 and the end housing portion 202. As discussed above, the expressing assembly 20 can hold at least two materials to be expressed at a selected time. The passages 212, 214 allow the materials to be passed through the tip portion 200 and mixed in the mixing area 223.

It will be understood that the mixing plate 220 can be provided according to various embodiments. For example, with reference to FIG. 6E, a mixing plate 220' is illustrated. The mixing plate 220' can be interconnected with the end housing portion 202, as discussed above, such as with sonic welding, adhesives, single piece molding, or any appropriate manner. In addition, the mixing plate 220' can be substantially similar to the mixing plate 220. The mixing plate 220', however, can include only three mixing channels 250, 251, 252 defined by only three walls 258, 259, 260. Materials expressed from both of the chambers of the expressing assembly 20 can still be mixed or combined, but only through the three distinct channels.

Figure 6F:
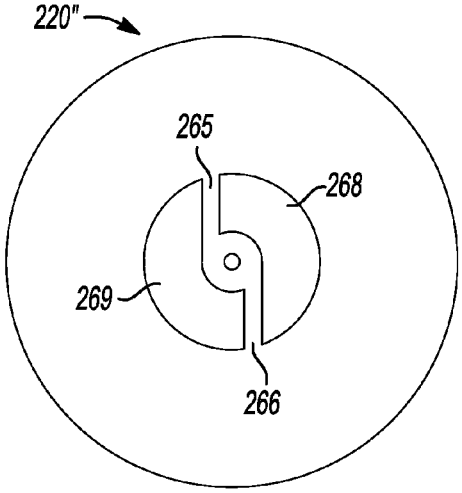

Additionally, a mixing plate 220" is illustrated in FIG. 6F. The mixing plate 220" can include only two channels 265, 266. These two channels 265, 266 can be defined by two directing walls 268, 269. It will be understood, therefore, that the mixing plates 220, 220', 220" can be provided in any appropriate manner and with any appropriate number of channels or directing walls. It will be understood that the illustrated mixing plates are merely exemplary. It will be further understood that a selected number of channels, such as a higher number of channels, can provide for substantially faster mixing or a greater amount of one of the materials from the expressing assembly 20 to be combined and/or mixed at a selected time. Accordingly, the volume of the channel, either alone or in total combination, can assist in determining or selecting an amount of the material to be mixed in the sump 240 for expression onto a selected cite.

The wall of the channels 232-238 can cause the material in the first chamber of the external container 22 to move in an agitated manner towards the central sump 240. The material from the second chamber, defined by the inner tube 37, can be expressed through the channel 214 substantially into the sump area 240. The convergence of the channels and the material from the second chamber can cause agitation within the sump 240 to assist in substantially mixing the materials before they are expressed through the expression port 242. Therefore, the two materials that are contained within the expressing assembly 20 can be substantially mixed prior to expression of the materials through the expression port 242.

In addition, the wall portions 224-230 defining the channels 232-238 can define the channels in a manner to assist in mixing the material. For example, the channels 232 can end in walls that include a radius 232a to assist in directing a material in a circular manner around the sump 240 to assist in mixing it with the material expressed from the second chamber defined by the inner tube 37. Accordingly, the tip portion 200 can be used to assist in substantially mixing the material prior to expression. Mixing a material prior to expression can assist in allowing for substantially fast acting material. For example, if thrombin and fibrinogen are mixed the tissue sealing properties of the mixture can be substantially instantaneous upon application to a selected area, such as during a procedure to close a wound. Therefore, the mixing tip portion 200 can be used in providing a substantially mixed material for expression by a user and substantially fast acting mixing.

Figure 6G:
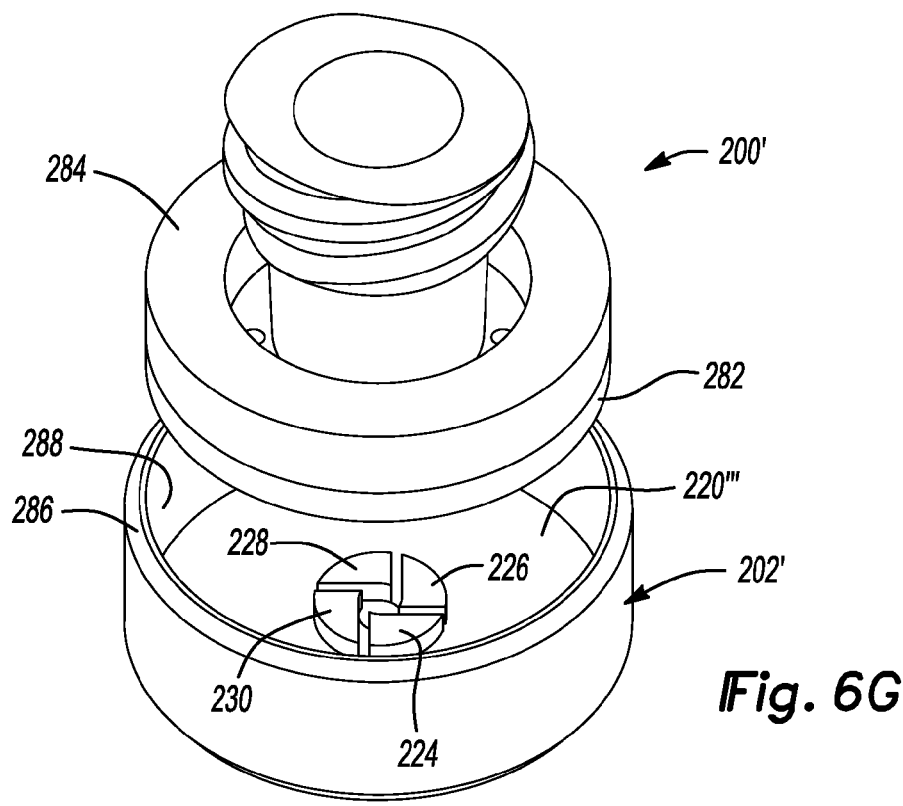
FIG. 6G is an exploded perspective view of a tip portion, according to various embodiments.
Figure 6H:
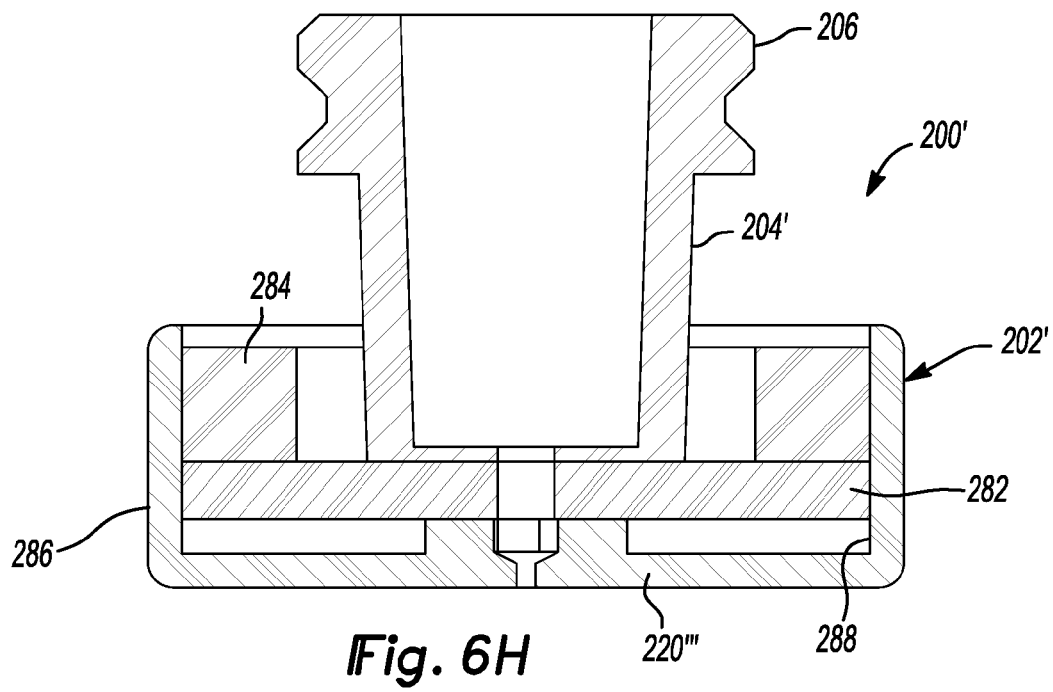
FIG. 6H is a cross-sectional view of a tip portion, according to various embodiments.

With reference to FIGS. 6G and 6H a tip portion 200' is illustrated. The tip portion 200' can be similar to the tip portion 200, but include a construction similar to the tip portion 120. The tip portion 200' can include an end housing 202' and a connecting portion 204' that can include a plate 282. To assist in sealing the tip portion 200' to the external housing 22 an O-ring or sealing member 284 can be provided to engage the plate 282 in the end housing 202'.

The end housing 202' can include a mixing plate 220''' and a sidewall 286 extending from the mixing plate 220'''. The sidewall 286 can include an interior wall 288 that can be connected with the plate 282 through any appropriate mechanism, such as welding, adhesives, molding, or the like. The mixing plate 220''' can have the mixing walls 224-230 extending therefrom. The mixing walls 224-230, as discussed above, can allow for mixing or combining of material from the expressing assembly 20 prior to it's expression from the tip portion 200'. The combination method can include the method as discussed above in the tip portion 200, although the assembly of the tip portion 200' maybe different from the tip portion 200.

With reference to FIGS. 7A-7C, a tip portion 300 is illustrated that includes a first tube member 302 and a second tube member 304 through which materials can be expressed. The first tube portion 302 can define a cannula 306 through which the second tube member or portion 304 can be positioned. The second tube member 304 can also define an internal cannula or passage 308. The two passages 306, 308 can be interconnected with the outlet portion 32 of the expressing assembly 20 to allow for expression of the two materials through the individual passages 306, 308 to a terminal end of the two tube members 302, 304 for delivery to a selected cite.

The two tube members 302, 304 can be formed of the same or different materials. Additionally, the two tube members 302, 304 can include the same or different characteristics. For example, the two tube members 302, 304 can be flexible, rigid, made of a memory material, or any other appropriate characteristics can be provided. In a further example, the inner tube 304 can be made from a rigid material, such as a metal or allow, and the exterior tube 306 can be made of a flexible material, such as a polymer.

It can also be selected to form the two tube members 302, 304 of different lengths. For example, the inner tube 304 can be formed at a shorter length than the outer tube member 302 such that the two materials can mix at any appropriate position within the outer tube 302 prior to being expressed to a selected cite. Alternatively, the inner tube 304 can be longer than the outer tube 302 for positioning the material within the inner chamber, defined by the inner tube 37 of the expressing assembly 20, to a selected cited prior to the second material. In addition, the inner tube member 304 can be perforated such that at least a portion of the material expressed through the inner tube 304 can be mixed with the material and the outer tube 302 prior to it being expressed out of the outer tube 302.

The cannula tip assembly 300 can include an end housing portion 320 and a connector portion 322. The connector portion 322 can include a locking or other appropriate thread or connection 324 to engage the threads 52 of the outlet portion 32. Again, the connection 324 can include a detent, as discussed above. The connecting portion 322 can also include an internal wall 326 to engage the external wall 56 of the external container 22 to provide a seal from the inner tube 37 of the external container 22 through the inner tube member 304. A second sealing portion, such as an o-ring 328, can be provided within the end housing portion 320 to seal the second area.

A first passage 330 can allow for expression of material from the first storage area within the syringe to a collection area 332 of the end housing portion and to an outlet 334 to allow the material to pass through the outer tube 302. A second passage 336 can be positioned substantially coaxially with the inner wall 326 to allow material held within the inner tube 37 of the external container 22 to be expressed through the second tube member 304 of the tip portion 300. Accordingly, material from both of the chambers of the expressing assembly 20 can be expressed substantially simultaneously through the tube or cannula tip portion 300.

The cannula tip portion 300 can allow for a substantially precise expression of material to a selected area. For example, during an operative procedure, a surgeon can select to precisely position material relative to a patient. It will also be understood that the cannula tip assembly 300 can be used to express the material, such as a two part industrial or construction adhesives substantially precise. It will be understood, therefore, that the expressing assembly 20 and the cannula tip portion 300 (or any tip portion, including those disclosed herein) is not necessarily restricted specifically to the use of a human tissue sealant.

The various assemblies discussed above, such as the expressing assembly 20, the sterile transfer assembly 100, the tip portions 120, 200, 300, according to various embodiments, can be used in any appropriate manner. One exemplary usage will be described and illustrated in FIGS. 8A-8C. According to various embodiments, autologous materials, such as whole blood can be withdrawn from a patient and separated and concentrated according to various characteristics. For example, whole blood can be separated in a centrifuge system with a separation assembly 400, as illustrated in FIG. 8A. The separation assembly 400 can be any appropriate assembly, such as the GPS III sold by Biomet Inc. having a place of business in Warsaw, Ind. The separation assembly 400 can separate a selected material, such as a whole blood, with a density or gravity tuned buoy 402 and a separator 404. Other appropriate assemblies are also disclosed in U.S. Pat. No. 7,374,678, issued on May 20, 2008 and U.S. patent application Ser. No. 12/101,586, filed on Apr. 11, 2008.

Once the material is separated, according to any appropriate mechanism such as the separation assembly 400, the material can be loaded into the expressing assembly 20 while it is positioned within the sterile package, as illustrated in FIG. 8B. Two syringes, such as the first syringe 88 and the second syringe 92 can be used to deliver a first and second material to the expressing assembly 20. The plungers 26, 39 can be drawn generally in the direction of arrow Z to fill the two chambers defined by the expressing assembly 20. The material can be expressed from the two syringes 88, 92 into the expressing assembly 20 substantially simultaneously. It will be understood that any appropriate users can fill the expressing assembly 20, such as a single or multiple users. Nevertheless, the use of the filling port 80 that is positioned within the sealing package 100 can allow for the substantially sterile filling of the expressing assembly 20.

As discussed above, the expressing assembly 20 can be filled while the expressing assembly 20 is within a container 100. It will be understood, however, that the expressing assembly 20 can be filled at any appropriate time and filling it within the container 100 is merely exemplary. According to various embodiments, a vial may be filled with a material and transferred in the sterile container 100 to a sterile field, rather than filling the expressing assembly 20. According to various embodiments, the filling port 80 can also be provided to span a non-sterile field (NSF) and a sterile field (SF), as illustrated in FIG. 8B'. When spanning an area between the NSF and the SF, a person M in the NSF can connect the filling syringes 88, 92 to the port 80 and a second user N can fill the expressing assembly 20 in the SF through the port 80. Once the expressing assembly 20 is filled, the person N in the SF can disconnect it from the port 80 and use the expressing assembly 20 within the SF. The expressing assembly 20, therefore, can be filled according to various embodiments in any appropriate manner prior to connection with a selected tip portion, as discussed herein.

In addition to using the port 80, two materials can be introduced into the expressing assembly 20 using the two syringes 88, 92 and connecting them directly to the outlet end 32. As illustrated in FIGS. 8B" and 8B"', the two syringes 88, 92 can be separately connected with the outlet end 32 and separately emptied into the expressing assembly 20.

For example, as illustrated in FIG. 8B", the first syringe 88 can be interconnected with the outlet end 32 and the second plunger 39 can be drawn in the direction of arrow B, while a plunger 88$p$ of the first syringe 88 is moved in the direction of arrow Z to fill the second chamber 38$a$ of the inner tube 37. The first syringe 88 can then be removed and the second syringe 92 can be interconnected with the outlet end 32 and the first plunger 26 can be moved in the direction of arrow Z, while a plunger 92$p$ of the second syringe 92 is moved in the direction of arrow Z to fill the first chamber 24. Accordingly, the port 80 may not be necessary to fill the expressing assembly 20 with two separate materials. Once filled, however, the expressing assembly 20 can be used to express materials with any of the tip portions, including those discussed above.

Once the expressing assembly 20 is filled, it can be transferred to a substantially sterile field using any appropriate procedure, such as the procedure discussed above. The sterile transfer procedure can allow the expressing assembly 20 to be filled in a substantially non-sterile area, such as an area where a centrifuge may be stored, and transferred back to a substantially sterile field. This can allow for efficient positioning of capital or large equipment, such as the centrifuge, and central processing of materials. Accordingly, a single or minimal number of trained individuals can be provided to separate blood materials while allowing for a sterile transfer of the blood materials back to a user for application to the patient.

Once the expressing assembly 20 has been disconnected from the transfer port assembly 80 and an appropriate tip portion 120, 200, 300 can be interconnected with the expressing assembly 20. As exemplary illustrated here, in FIG. 8C, the expressing assembly 20 can be interconnected with the non-mixing tip portion 120. As discussed above, the first material 406 can be positioned in a first area of the expressing assembly 20 while the second material 408 can be positioned within the inner tube member 37 of the expressing assembly 20. As illustrated in FIG. 8C, the material can be maintained substantially separate until the material is expressed into the non-mixing portion 120 and out the exit ports 150, 154.

As discussed above, the exit ports 150, 154 can be formed to form a substantially conical spray of material including a first cone 154a and a second cone 150a that mix at a selected point at a selected amount, such as a mixture area 410. The mixture amount can be any appropriate amount, but can be expressed onto an incision 412 formed within a patient 414. For example, the incision 412 can be an incision provided to allow for insertion of a femoral hip implant 416. The material that is expressed in cones 150a, 154a can include a tissue sealant including thrombin extracted and concentrated from the patient 414. Accordingly, a substantially autologous tissue sealant can be provided to the patient 414 to assist in healing, including speed healing of the incision 412. It will be understood that any appropriate tip portion can also be used for expressing the material relative or onto the incision 412 and the non-mixing tip portion 120 is illustrated in FIG. 8C merely for example purposes.

The materials remain separated within the expressing assembly 20 can be both substantially autologously extracted from the patient 414 or it can include one autologous component and one non-autologous component. In addition, both of the materials can be non-autologous and can be either man-made or natural materials. The materials can include, for example, pooled human and animal substances and derived substances. Nevertheless, the expressing assembly 20 can allow a user to express material onto the patient 414 at any appropriate time for any appropriate purpose, such as tissue sealant. In addition any appropriate tip portion, including the tip portions 120, 200, 300 discussed above, can be selected by a user to achieve appropriate purposes. As discussed above, mixing the materials prior to expression can be selected for allowing a substantially mixed material being applied to the patient 414. The tube tip portion 300, however, can be selected to provide a substantially precise positioning of a mixed or unmixed material. Therefore, it will be understood that a user can select any appropriate tip portion for interconnection with the expressing assembly 20.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of expressing a material to a selected site from an expressing assembly having a first chamber and a second chamber, wherein a first material in the first chamber is separated from a second material in the second chamber before expression of the first material and the second material from the respective first chamber and second chamber, comprising:
connecting a tip portion with the expressing assembly to form an extension of a first passage between a female connection portion of the expressing assembly or the tip portion and a male connection portion of the other of the expressing assembly or the tip portion;
contacting a sealing member with the connected tip portion to seal the first chamber of the expressing assembly with the extension of the first passage;
expressing the first material and the second material through the connected tip portion; and
forming the material by mixing the first material and the second material in the connected tip portion before the material exits the connected tip portion, wherein mixing includes using a mixing plate that forms a portion of the connected tip portion and is connected with an end housing portion of the connected tip portion.

2. The method of claim 1, further comprising:
directing the first material through the connected tip portion to form a first cone separate from a second cone formed by directing the second material through the connected tip portion; and
causing the first cone and the second cone to intersect external to the connected tip portion.

3. The method of claim 1, further comprising:
collecting a first volume of the first material in a first collection volume of the connected tip portion when the first material is expressed from the expressing assembly;
wherein expressing the second material through the connected tip portion includes expressing the second material through a first tube positioned with the connected tip portion to extend substantially directly from the second chamber;
wherein expressing the first material through the connected tip portion includes expressing the first volume from the first collection volume through a second tube coaxial around the first tube.

4. The method of claim 1, further comprising:
providing a second passage of the tip portion, wherein expressing the first material and the second material includes expressing at least one of the first material and the second material through the second passage.

5. The method of claim 1, wherein the tip portion comprises a first tube having a first tube length, and a second tube having a second tube length, the first tube length being different from the second tube length.

6. The method of claim 5, wherein the first tube and the second tube are coaxial.

7. The method of claim 5, wherein forming the material includes allowing one of the first material or the second material to exit through at least one perforation in a wall of the connected tip portion to mix with the other of the first material and the second material.

8. The method of claim 1, wherein the tip portion comprises a first expression port and a second expression port, and forming the material includes expressing the material formed by mixing the first material and the second material through the first expression port and the second expression port of the connected tip portion.

9. The method of claim 8, wherein the material is expressed from at least one of the first expression port and the second expression port at an angle between 45° and 170°.

10. The method of claim 1, wherein forming the material includes forming a first cone of the material expressed through a first expression port, forming a second cone of the material expressed through a second expression port, and intersecting the first cone and the second cone.

11. The method of claim 1, wherein mixing the first material and the second material using the mixing plate includes passing the first material and the second material, respectively, through at least a first channel and a second channel of the mixing plate.

12. The method of claim 1, wherein mixing the first material and the second material includes passing the first material and the second material to a sump of the connected tip portion.

13. The method of claim 12, wherein the sump comprises an angle between 45° and 170°.

14. The method of claim 1, wherein mixing the first material and the second material includes forming a confluence or agitation in the first material, the second material, or both.

15. The method of claim 1, wherein expressing the first material and the second material includes expressing the first material through the connected tip portion independent of expressing the second material through the connected tip portion.

16. The method of claim 1, wherein expressing the first material and the second material includes expressing a volume of the first material through the connected tip portion that is different from a volume of the second material expressed through the connecting tip portion.

17. The method of claim 1, wherein expressing the first material and the second material includes expressing the first material through the connected tip portion at a rate that is different from a rate at which the second material is expressed through the connected tip portion.

18. The method of claim 1, further comprising:
providing a first plunger configured to be received within the first chamber and a second plunger configured to be received with the second chamber, wherein expressing the first material and the second material includes permitting the first plunger and the second plunger to independently express, respectively, the first material and the second material through the connected tip portion.

19. The method of claim 1, wherein forming the material includes selecting a volume of the first material to be mixed with a selected volume of the second material.

20. The method of claim 1, wherein forming the material includes substantially mixing the first material and the second material in a sump of the connected tip portion before the material exits the connected tip portion.

\* \* \* \* \*